US007705151B2

(12) United States Patent
Cywin et al.

(10) Patent No.: US 7,705,151 B2

(45) Date of Patent: Apr. 27, 2010

(54) 1,6 NAPHTHRIDINES USEFUL AS INHIBITORS OF SYK KINASE

(75) Inventors: Charles L. Cywin, Bethel, CT (US); Scott E. Jakes, Southbury, CT (US); Joachim Heider, Warthausen (DE); Mark A. Bobko, Exton, PA (US); Renee L. Des Jarlais, St. Davids, PA (US); Mark Player, Phoenixville, PA (US); James Rinker, Reading, PA (US); Michael Winters, Lancaster, PA (US); Bao-ping Zhao, West Windsor, NJ (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 12/399,292

(22) Filed: Mar. 6, 2009

(65) Prior Publication Data

US 2009/0171089 A1 Jul. 2, 2009

Related U.S. Application Data

(60) Division of application No. 12/014,190, filed on Jan. 15, 2008, which is a continuation of application No. 10/413,980, filed on Apr. 15, 2003, now Pat. No. 7,321,041, which is a continuation of application No. 10/029,714, filed on Dec. 21, 2001, now abandoned.

(51) Int. Cl.
*C07D 471/02* (2006.01)
*C07D 413/00* (2006.01)

(52) U.S. Cl. ...................................... 546/122; 544/127

(58) Field of Classification Search .................. 546/122
See application file for complete search history.

(56) References Cited

U.S. PATENT DOCUMENTS

| | | | | |
|---|---|---|---|---|
| 4,107,166 | A | 8/1978 | Mayer et al. | |
| 4,260,759 | A | 4/1981 | Mayer et al. | |
| 6,340,759 | B1 | 1/2002 | Ueno et al. | |
| 7,321,041 | B2 * | 1/2008 | Cywin et al. | 546/122 |

FOREIGN PATENT DOCUMENTS

| | | | |
|---|---|---|---|
| EP | 1 020 445 | A1 | 7/2000 |
| WO | 99/18077 | A1 | 4/1999 |
| WO | 01/09134 | A1 | 2/2001 |
| WO | 01/47922 | A2 | 7/2001 |
| WO | 01/47922 | A3 | 7/2001 |
| WO | 02/22601 | A1 | 3/2002 |

OTHER PUBLICATIONS

Atkins, Fred M; Intestinal Mucosal Mast Cells; Annals of Allergy (1987) vol. 59 pp. 44-53.

Claman, Henry N; On Scleroderma: Mast Cells, Endothelial Cells, and Fibroblasts; JAMA (1989) vol. 262, No. 9 pp. 1206-1209.

Crowe, Sheila E., et al; Functional Abnormalities in the Intestine Associated with Mucosal Mast Cell Activation; Regional Immunology (1992) vol. 4 pp. 113-117.

Graziano, Frank M., et al; Conjunctival Mast Cells in Ocular Allergic Disease; Allergy and Asthma Proc (2001) vol. 22, No. 3 pp. 121-126.

Kraft, Stefan, et al; Unexpected Functions of FcεRI on Antigen-Presenting Cellls; International Archives of Allergy and Immunology (2001) vol. 124 pp. 35-37.

Turner, Martin, et al; Tyrosine Kinase SYK: Essential Functions for Immunoreceptor Signalling: immunology Today (2000) vol. 21, No. 3 pp. 148-154.

Oliver, Janet M., et al; immunologically Mediated Signaling in Basophils and Mats Cells: Finding Therapeutic Targets for Allergic Diseases in the Human FcεR1 Signaling Pathway.

Wermuth et al; "The Practice of Medicinal Chemistry","Molecular Variations Based on Isosteric Replacements,", 1996 Academic Press Limited, pp. 203-237.

Ulanova et al; Spleen Tyrosine Kinase (SYK) as a Novel Target for Allergic Asthma and Rhinitis; Expert Opinion; Ther Targets (2005) 9(5) pp. 901-921.

Cywin et al; Discovery & SAR of Novel 1,6 Naphthyridines as Potent Inhibitors of Spleen Tyrosine Kinase (SYK); Bioorganic & Medicinal Chemistry Letters (2003) vol. 13 pp. 1415-1418.

LeCointe; Reach-Through Claims; International Pharmaceutical (2002) (also available at: http://www.bakerbotts.com/infocenter/publications/detail.aspx?id=bffe4a7d-5beb-4cf8-a189-15a5f190f0eb).

Silva; Reach-Through Claims; Bust or Boon? Intellectual Property Update (available at: http://www.dorsey.com/publications/legal_detail.aspx?FlashNavID=pubs_legal&pubid=170565003).

* cited by examiner

*Primary Examiner*—D. Margaret Seaman
*Assistant Examiner*—Nizal S Chandrakumar
(74) *Attorney, Agent, or Firm*—Michael P. Morris

(57) ABSTRACT

Disclosed are compounds of formula (I):

I $R_5$, $R_3$, N, N, $R_7$, $R_8$ wherein $R_3$, $R_5$, $R_7$ and $R_8$ are defined herein, which are useful as inhibitors SYK kinase and are thus useful for treating diseases resulting from inappropriate mast cell activation, which include allergic and inflammatory diseases. Also disclosed are pharmaceutical compositions comprising these compounds and processes for preparing these compounds.

2 Claims, No Drawings

1,6 NAPHTHRIDINES USEFUL AS INHIBITORS OF SYK KINASE

Related Applications

The present application is a division of U.S. patent application No. 12/014,190 filed Jan. 15, 2008, now allowed, which is a continuation of U.S. patent application Ser. No. 10/413,980, filed April, 15, 2003, now U.S. Pat. No. 7,321, 041, which is a continuation U.S. patent application Ser. No. 10/029,714, filed Dec. 21, 2001, (now abandoned), the contents of each of which is hereby incorporated by reference in their entirety.

TECHNICAL FIELD OF THE INVENTION

This invention relates to substituted [1,6]-naphthyridines that inhibit SYK kinase. In one embodiment, this invention relates to a novel class of substituted [1,6]-naphthyridines and pharmaceutical compositions comprising these compounds. This invention also relates to methods for producing such novel [1,6]-naphthyridines. Because of the ability of these compounds to inhibit SYK kinase, the compounds and pharmaceutical compositions of this invention are particularly well suited for preventing and treating inflammatory and allergic diseases.

BACKGROUND OF THE INVENTION

Mast cells play a critical role in asthma and allergic disorders by releasing pro-inflammatory mediators and cytokines. Antigen-mediated aggregation of Fc$\epsilon$RI, the high-affinity receptor for IgE results in activation of mast cells. This triggers a series of signaling events resulting in the release of mediators, including histamine, proteases, leukotrienes and cytokines. These mediators cause increased vascular permeability, mucus production, bronchoconstriction, tissue degradation and inflammation, thus playing key roles in the etiology and symptoms of asthma and allergic disorders.

One of the key events in the signaling pathway following the activation of mast cells is activation of the tyrosine kinase SYK. SYK kinase acts as a central initiator of all subsequent signaling leading to mediator release. The critical role of SYK kinase in the signaling path was demonstrated by the complete inhibition of mediator release by a protein containing the SH2 domains of SYK kinase that functioned as an inhibitor of SYK kinase (J. A. Taylor et al., Molec. and Cell Biol., 1995, 15, 4149). Furthermore, direct clustering of SYK, introduced into a mast cell line as part of a chimeric transmembrane protein, was found to be sufficient to stimulate the events leading to mediator release normally induced by clustering of Fc$\epsilon$RI (V. M. Rivera and J. S. Brugge, Molec. and Cell. Biol., 1995, 15, 1582).

ER-27319 (3,4-dimethyl-10-(3-aminopropyl)-9-acridone oxalate), a compound reported to interfere with the activation of SYK, has been shown to inhibit anti-IgE mediated degranulation in rodent and human mast cells (K. Moriya et al., Proc. Nat. Acad. Sci. USA, 1997, 94, 12539). Concentrations of piceatannol (3,4,3'5'-tetrahydroxy-trans-stilbene), a non-selective SYK kinase inhibitor, that inhibited the antigen-stimulated phosphorlation of SYK also inhibited functional responses in mast cells, including mediator release (J. M. Oliver et. al., J. Biol. Chem., 1994, 269, 29697).

The conclusion from the studies described above is that SYK kinase activation and activity is required for Fc$\epsilon$RI-mediated release of mediators from mast cells. Therefore, agents that block the activity of SYK kinase act to block the release of allergic and pro-inflammatory mediators and cytokines. These agents have potential utility in treating inflammatory and allergic disorders including asthma, chronic obstructive pulmonary disease (COPD), adult respiratory distress syndrome (ARDS), ulcerative colitis, Crohn's disease, bronchitis, conjunctivitis, psoriasis, scleroderma, urticaria, dermatitis and allergic rhinitis.

In addition to the inhibitors mentioned above, WO 0109134 discloses purine derivatives as inhibitors of SYK kinase. WO 9931073 describes pyrimidine -5-carboxamide derivatives as inhibitors of SYK kinase. WO 0147922 describes substituted azaindoles useful in the treatment of disease states capable of being modulated by the inhibition of protein kinases, in particular SYK kinase. WO 9818782 describes inhibitors of ZAP70 that are also reported to inhibit SYK.

In addition to mast cells, SYK is expressed in other hematopoietic cells including B cells, where it is thought to play an essential role in transducing signals required for the transition of immature B cells into mature recirculating B cells (M. Turner et al., Immunology Today, 2000, 21, 148). B cells are reported to play an important role in some inflammatory conditions such as lupus (O. T. Chan et al., Immunological Rev., 1999, 169, 107) and rheumatoid arthritis (A. Gause and C. Borek, Biodrugs, 2001, 15, 73).

SYK was also reported to be an element of the signaling cascade in beta-amyloid and prion fibrils leading to production of neurotoxic products (C. K. Combs et al., J. Neurosci., 1999, 19, 928). Furthermore, an inhibitor of SYK blocked the production of these neurotoxic products. Thus a SYK inhibitor would potentially be useful in the treatment of Alzheimer's disease and related neuroinflammatory diseases. Another report (Y. Kuno et al., Blood, 2001, 97, 1050) demonstrates that SYK plays an important role in malignant progression. A TEL-SYK fusion protein was found to transform hematopoietic cells suggesting a role in the pathogenesis of hematopoietic malignancies. Therefore a SYK inhibitor may be useful in the treatment of certain types of cancers.

A recent report suggests that SYK is a mediator of epithelial cell growth and suggests that it could be a potential tumor-suppressor in human breast carcinomas (P. J. P. Coopman et al., Nature, 2000, 406, 742). One could conclude from this report that while inhibition of SYK kinase activity could be desirable for treatment of inflammatory and allergic disease and asthma, a complete, irreversible blockade of SYK kinase activity may not be desirable.

BE 835,770 describes 5-amino-1,6-naphthyridines having antimicrobial activity. U.S. Pat. No. 3,928,367, U.S. Pat. No. 4,017,500, U.S. Pat. No. 4,115,395 and U.S. Pat. No. 4,260, 759 describe 5-amino-1,6-naphthyridines having antifungal and antibacterial activity. WO 9918077 describes 5-piperazinyl-1,6-naphthyridines as serotonin antagonists.

BRIEF DESCRIPTION OF THE INVENTION

The work cited above supports the principle that inhibition of SYK kinase will be beneficial in the treatment of various disease states. It is therefore an object of the invention to provide novel compounds which inhibit SYK kinase It is a further object of the invention to provide methods for treating diseases and pathological conditions mediated by SYK kinase such as inflammatory and allergic disorders including asthma, chronic obstructive pulmonary disease (COPD), adult respiratory distress syndrome (ARDS), ulcerative colitis, Crohn's disease, bronchitis, conjunctivitis, psoriasis, scleroderma, urticaria, dermatitis allergic rhinitis, lupus and rheumatoid arthritis using the novel compounds of the invention.

It is yet a further object of the invention to provide processes of preparation for the above-mentioned novel compounds and pharmaceutical compositions comprising the same.

DETAILED DESCRIPTION OF THE INVENTION

In its broadest generic aspect, the invention provides novel compounds of the formula (I) below:

(I)

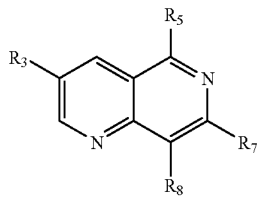

wherein:

$R_3$ is H, $C_{1-3}$alkyl, halogen or phenyl;

$R_5$ is $N(R_9)(R_{10})$ or $OR_{11}$ wherein $R_9$ is H or $C_{1-3}$alkyl, $R_{10}$ is amino$C_{2-6}$alkyl, $C_{1-4}$alkylamino$C_{2-6}$alkyl, di$C_{1-4}$ alkylamino$C_{2-6}$alkyl, $C_{1-4}$alkoxy$C_{2-6}$alkyl or hydroxy $C_{2-6}$alkyl, wherein one methylene group in said $C_{2-6}$alkyl is optionally replaced with an oxygen, sulfur, NH, or $NCH_3$, and wherein each methylene group in said $C_{2-6}$alkyl is optionally substituted with a halogen, cyano or hydroxy group, or $R_{10}$ is $C_{3-7}$cycloalkyl, heterocycloalkyl, heteroaryl, $C_{3-7}$cycloalkyl$C_{1-4}$alkyl, heterocycloalkyl$C_{1-4}$alkyl, aryl$C_{1-4}$alkyl or heteroaryl$C_{1-4}$ alkyl each optionally substituted with one or more $C_{1-4}$alkyl, amino, $C_{1-4}$alkylamino, di$C_{1-4}$alkylamino, amino$C_{1-3}$alkyl, $C_{1-4}$alkylamino$C_{1-3}$alkyl, di$C_{1-4}$alkylamino$C_{1-3}$alkyl, halogen, hydroxy, aminocarboxy or benzyl groups, or $R_9$ and $R_{10}$ together with the nitrogen they are bonded to may form a heterocycloalkyl group containing one or more heteroatoms which is optionally substituted with one or more $C_{1-4}$alkyl, amino, $C_{1-4}$alkylamino, di$C_{1-4}$alkylamino, amino$C_{1-3}$alkyl, $C_{1-4}$alkylamino$C_{1-3}$alkyl, di$C_{1-4}$alkylamino$C_{1-3}$alkyl, halogen, hydroxy, aminocarboxy or benzyl groups, and $R_{11}$ is amino$C_{2-6}$alkyl, $C_{1-4}$alkylamino$C_{2-6}$alkyl, di$C_{1-4}$ alkylamino$C_{2-6}$alkyl, $C_{1-4}$alkoxy$C_{2-6}$alkyl or hydroxy $C_{2-6}$alkyl, wherein one methylene group in said $C_{2-6}$alkyl is optionally replaced with an oxygen, sulfur, NH, or $NCH_3$, and wherein each methylene group in said $C_{2-6}$alkyl is optionally substituted with a halogen, cyano or hydroxy group, or $R_{11}$ is $C_{3-7}$cycloalkyl, heterocycloalkyl, heteroaryl, $C_{3-7}$cycloalkyl$C_{1-4}$alkyl, heterocycloalkyl$C_{1-4}$alkyl, aryl$C_{1-4}$alkyl or heteroaryl$C_{1-4}$ alkyl each optionally substituted with one or more $C_{1-4}$alkyl, amino, $C_{1-4}$alkylamino, di$C_{1-4}$alkylamino, amino$C_{1-3}$alkyl, $C_{1-4}$alkylamino$C_{1-3}$alkyl, di$C_{1-4}$alkylamino$C_{1-3}$alkyl, halogen, hydroxy, aminocarboxy or benzyl groups;

$R_7$ is phenyl, naphthyl, furyl, thienyl, pyridyl, indolyl, benzothiazolyl or pyrrolyl optionally substituted with one or more $C_{1-3}$alkoxy, halogen, $CF_3$, $CF_3O$, hydroxy, $C_{1-3}$alkyl, amino, $C_{1-3}$alkylamino, di$C_{1-3}$alkylamino, $C_{1-3}$alkylamino$C_{1-3}$alkyl, di$C_{1-3}$alkylamino$C_{1-3}$alkyl, ($C_{1-3}$alkylamino$C_{1-3}$alkyl)($C_{0-3}$alkyl)amino, (di$C_{1-3}$alkylamino$C_{1-3}$ alkyl)($C_{0-3}$alkyl)amino, $C_{1-3}$alkylthio, aminocarboxy, $C_{1-3}$alkylcarbonyl, ureido optionally substituted with $C_{1-3}$alkyl, C(O)OC $_{1-4}$alkyl, C(O)OH , acetamido or heterocycloaklyl groups, or with a phenyl group which is optionally substituted with one or more $C_{1-3}$alkoxy, halogen, $CF_3$, $CF_3O$, hydroxy, $C_{1-3}$alkyl, amino, $C_{1-3}$alkylamino, di$C_{1-3}$alkylamino, $C_{1-3}$alkylamino$C_{1-3}$alkyl, di$C_{1-3}$ alkylamino$C_{1-3}$alkyl, $C_{1-3}$alkylthio, aminocarboxy, $C_{1-3}$alkylcarbonyl, ureido optionally substituted with $C_{1-3}$alkyl, C(O)O$C_{1-4}$alkyl, C(O)OH, acetamido, heteroaryl or heterocycloalkyl groups; and $R_8$ is H, halogen or cyano.

In another embodiment of the invention, there are provided compounds of the formula (I) as described immediately above, and wherein:

$R_3$ is H or methyl;

$R_5$ is $N(R_9)(R_{10})$ or $OR_{11}$ wherein $R_9$ is H or methyl, $R_{10}$ is amino$C_{2-6}$alkyl, $C_{1-4}$alkylamino$C_{2-6}$alkyl, di$C_{1-4}$ alkylamino$C_{2-6}$alkyl, $C_{1-4}$alkoxy$C_{2-6}$alkyl or hydroxy$C_{2-6}$alkyl, wherein one methylene group in said $C_{2-6}$alkyl is optionally replaced with an oxygen, sulfur, NH, or $NCH_3$, and wherein each methylene group in said $C_{2-6}$alkyl is optionally substituted with a halogen, cyano or hydroxy group, or $R_{10}$ is $C_{4-7}$cycloalkyl, heterocycloalkyl selected from pyrrolidinyl and piperidinyl, heteroaryl selected from oxazolyl, isoxazolyl, pyridyl and pyrimidinyl, $C_{3-6}$cycloalkyl$C_{1-4}$alkyl, heterocycloalkyl$C_{1-4}$alkyl wherein said heterocycloalkyl is selected from morpholinyl, pyrrolidinyl, pyrrolidin-2-onyl, piperidinyl, tetrahydrofuranyl and piperazinyl, phenyl$C_{1-4}$alkyl or heteroaryl$C_{1-4}$alkyl wherein said heteroaryl is selected from pyridyl, furyl, and imidazolyl, each optionally substituted with one or more $C_{1-4}$alkyl, amino, $C_{1-4}$alkylamino, di$C_{1-4}$alkylamino, amino$C_{1-3}$alkyl, $C_{1-4}$alkylamino$C_{1-3}$alkyl, di$C_{1-4}$alkylamino$C_{1-3}$alkyl, halogen, hydroxy, aminocarboxy or benzyl groups, or $R_9$ and $R_{10}$ together with the nitrogen they are bonded to may form a heterocycloalkyl group selected from piperidinyl, piperazinyl, pyrrolidinyl and morpholinyl which is optionally substituted with one or more $C_{1-4}$alkyl, amino, $C_{1-4}$alkylamino, di$C_{1-4}$alkylamino, amino$C_{1-3}$alkyl, $C_{1-4}$alkylamino$C_{1-3}$alkyl, di$C_{1-4}$alkylamino$C_{1-3}$alkyl, halogen, hydroxy, aminocarboxy or benzyl groups, and $R_{11}$ is is amino$C_{2-6}$alkyl, $C_{1-4}$alkylamino$C_{2-6}$alkyl, di$C_{1-4}$ alkylamino$C_{2-6}$alkyl, $C_{1-4}$alkoxy$C_{2-6}$alkyl or hydroxy $C_{2-6}$alkyl, wherein one methylene group in said $C_{2-6}$alkyl is optionally replaced with an oxygen, sulfur, NH, or $NCH_3$, and wherein each methylene group in said $C_{2-6}$alkyl is optionally substituted with a halogen, cyano or hydroxy group, or $R_{11}$ is $C_{5-7}$cyclohexyl, heterocycloalkyl selected from pyrrolidinyl and piperidinyl, heteroaryl selected from oxazolyl, isoxazolyl, pyridyl and pyrimidinyl, $C_{3-6}$cycloalkyl$C_{1-4}$alkyl, heterocycloalkyl$C_{1-4}$alkyl wherein said heterocycloalkyl is selected from morpholinyl, pyrrolidinyl, pyrrolidin-2-onyl, piperidinyl, tetrahydrofuranyl and piperazinyl, phenyl$C_{1-4}$alkyl or heteroaryl$C_{1-4}$alkyl wherein said heteroaryl is selected from pyridyl, furyl, and imidazolyl, each optionally substituted with one or more $C_{1-4}$alkyl, amino, $C_{1-4}$alkylamino, di$C_{1-4}$alkylamino, amino$C_{1-3}$alkyl, $C_{1-4}$alkylamino$C_{1-3}$alkyl, di$C_{1-4}$alkylamino$C_{1-3}$alkyl, halogen, hydroxy, aminocarboxy or benzyl groups;

$R_7$ is phenyl, naphthyl, furyl, thienyl, pyridyl, indolyl, benzothiazolyl or pyrrolyl optionally substituted with one or more $C_{1-3}$alkoxy, halogen, $CF_3$, $CF_3O$, hydroxy, $C_{1-3}$alkyl, amino, $C_{1-3}$alkylamino, di$C_{1-3}$alkylamino, $C_{1-3}$alkylamino$C_{1-3}$alkyl, di$C_{1-3}$alkylamino$C_{1-3}$alkyl, ($C_{1-3}$alkylamino$C_{1-3}$alkyl)($C_{0-3}$alkyl)amino, (di$C_{1-3}$alkylamino$C_{1-3}$ alkyl)($C_{0-3}$alkyl)amino, $C_{1-3}$alkylthio, aminocarboxy, ureido optionally substituted with $C_{1-3}$alkyl, acetamido or heterocycloalkyl groups, or with a phenyl group which is optionally substituted with one or more $C_{1-3}$alkoxy, halogen, $CF_3$, $CF_3O$, hydroxy, $C_{1-3}$alkyl, amino, $C_{1-3}$alkylamino, di$C_{1-3}$alkylamino, $C_{1-3}$alkylamino$C_{1-3}$alkyl, di$C_{1-3}$alkylamino$C_{1-3}$alkyl, $C_{1-3}$alkylthio, aminocarboxy, $C_{1-3}$alkylcarbonyl, ureido optionally substituted with $C_{1-3}$alkyl, C(O)O$C_{1-4}$alkyl, C(O)OH, acetamido, heteroaryl or heterocycloalkyl groups; and $R_8$ is H.

In another embodiment of the invention there are provided compounds of the formula (I) as described immediately above, and wherein:

$R_5$ is $N(R_9)(R_{10})$ or $OR_{11}$ wherein $R_9$ is H or methyl, $R_{10}$ is amino$C_{2-6}$alkyl, methylamino$C_{2-6}$alkyl, dimethylamino$C_{2-6}$alkyl, methoxy$C_{2-6}$alkyl or hydroxy$C_{2-6}$ alkyl, wherein one methylene group in said $C_{2-6}$alkyl is optionally replaced with an oxygen or sulfur, and wherein each methylene group in said $C_{2-6}$alkyl is optionally substituted with a hydroxy group, or $R_{10}$ is $C_{4-7}$cycloalkyl, heterocycloalkyl selected from pyrrolidinyl and piperidinyl, heteroaryl selected from oxazolyl, isoxazolyl, pyridyl and pyrimidinyl, $C_{3-6}$cycloalkyl$C_{1-4}$alkyl, heterocycloalkyl$C_{1-4}$alkyl wherein said heterocycloalkyl is selected from, pyrrolidin-2-only and piperidinyl, benzyl or heteroaryl$C_{1-4}$alkyl wherein said heteroaryl is selected from pyridyl and imidazolyl, each optionally substituted with one or more amino, aminomethyl, methylaminomethyl, dimethylaminomethyl, hydroxy, aminocarboxy or benzyl groups, or $R_9$ and $R_{10}$ together with the nitrogen they are bonded to may form a heterocycloalkyl group selected from piperidinyl, piperazinyl, pyrrolidinyl and morpholinyl which is optionally substituted with one or more amino, hydroxy or aminocarboxy groups, and $R_{11}$ is amino$C_{2-6}$alkyl, methylamino$C_{2-6}$alkyl, dimethylamino$C_{2-6}$alkyl, methoxy$C_{2-6}$alkyl or hydroxy$C_{2-6}$ alkyl, wherein one methylene group in said $C_{2-6}$alkyl is optionally replaced with an oxygen or sulfur, and wherein each methylene group in said $C_{2-6}$alkyl is optionally substituted with a hydroxy group, or $R_{11}$ is $C_{5-7}$cycloalkyl, heterocycloalkyl selected from pyrrolidinyl and piperidinyl, heteroaryl selected from oxazolyl, isoxazolyl, pyridyl and pyrimidinyl, $C_{3-6}$cycloalkyl$C_{1-4}$alkyl, heterocycloalkyl$C_{1-4}$alkyl wherein said heterocycloalkyl is selected from, pyrrolidin-2-only and piperidinyl, benzyl or heteroaryl$C_{1-4}$alkyl wherein said heteroaryl is selected from pyridyl and imidazolyl, each optionally substituted with one or more amino, aminomethyl, hydroxy, aminocarboxy, benzyl, methylaminomethyl, or dimethylaminomethyl groups;

$R_7$ is phenyl, optionally substituted in the 3-, 4- or 5-positions with one or more methoxy, fluorine, chlorine, bromine, $CF_3$, $CF_3O$, $C_{1-3}$alkyl, di$C_{1-3}$alkylamino, di$C_{1-3}$alkylamino$C_{1-3}$alkyl, ($C_{1-3}$alkylamino$C_{1-3}$alkyl)($C_{0-3}$alkyl)amino, (di$C_{1-3}$alkylamino$C_{1-3}$alkyl)($C_{0-3}$alkyl)amino, thiomethoxy, acetamido, 4-morpholinyl, 1-piperidinyl or 1-pyrrolidinyl groups, or substituted in the 4-position with a phenyl group optionally substituted in the 4-position with a methyl, methoxy, 2-thienyl or 3-pyridyl group, or $R_7$ is a 2-naphthyl or 2-thienyl group or a 5-indoyl group optionally substituted in the 1-position with a $CF_3$, $C_{1-3}$alkyl, di$C_{1-3}$alkylamino$C_{1-3}$alkyl, or $C_{1-3}$alkylamino$C_{1-3}$alkyl group; and $R_8$ is H.

In yet another embodiment of the invention there are provided compounds of the formula (I) as described immediately above, and wherein:

$R_3$ is H;

$R_5$ is $N(R_9)(R_{10})$ or $OR_{11}$ wherein $R_9$ is H or methyl, $R_{10}$ is amino$C_{3-4}$alkyl or hydroxy$C_{3-4}$alkyl wherein each methylene group in said $C_{3-4}$alkyl is optionally substituted with a hydroxy group, or $R_{10}$is $C_{5-7}$cycloalkyl substituted with an amino or hydroxy group, and $R_{11}$ is amino$C_{3-4}$alkyl or hydroxy$C_{3-4}$alkyl wherein each methylene group in said $C_{3-4}$alkyl is optionally substituted with a hydroxy group, or $R_{11}$ is $C_{5-7}$cycloalkyl substituted with an amino or hydroxy group;

$R_7$ is phenyl, substituted in the 4-position with a di$C_{1-2}$alkylamino, (dimethylamino$C_{2-3}$alkyl)($C_{0-3}$alkyl)amino, isopropyl, 4-morpholinyl, 4-piperidinyl or 4-pyrrolidinyl group and optionally substituted in the 3-position with a chlorine, bromine or methoxy group; and $R_8$ is H.

In a further embodiment of the invention, there are provided the following compounds:

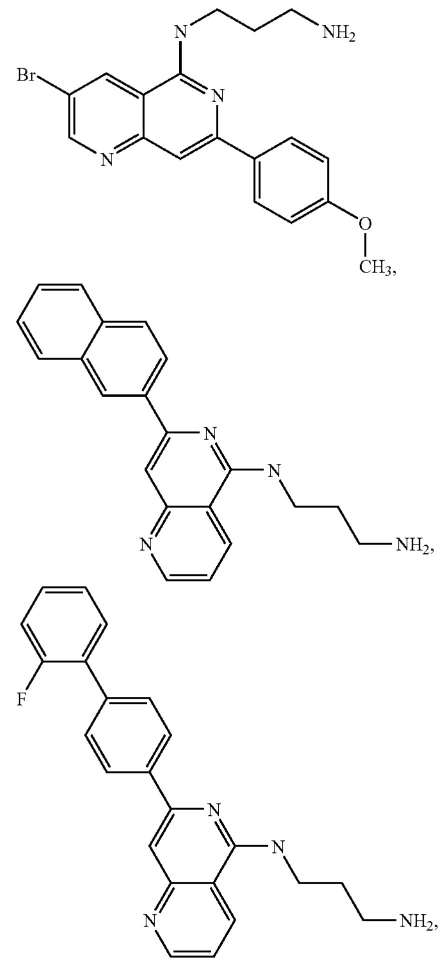

-continued
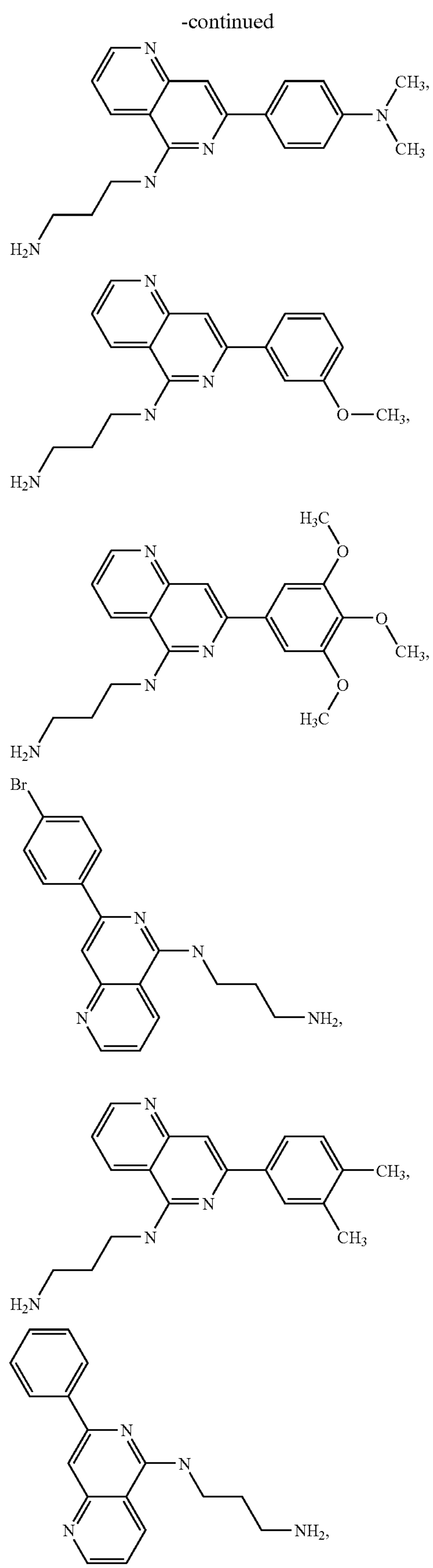
-continued
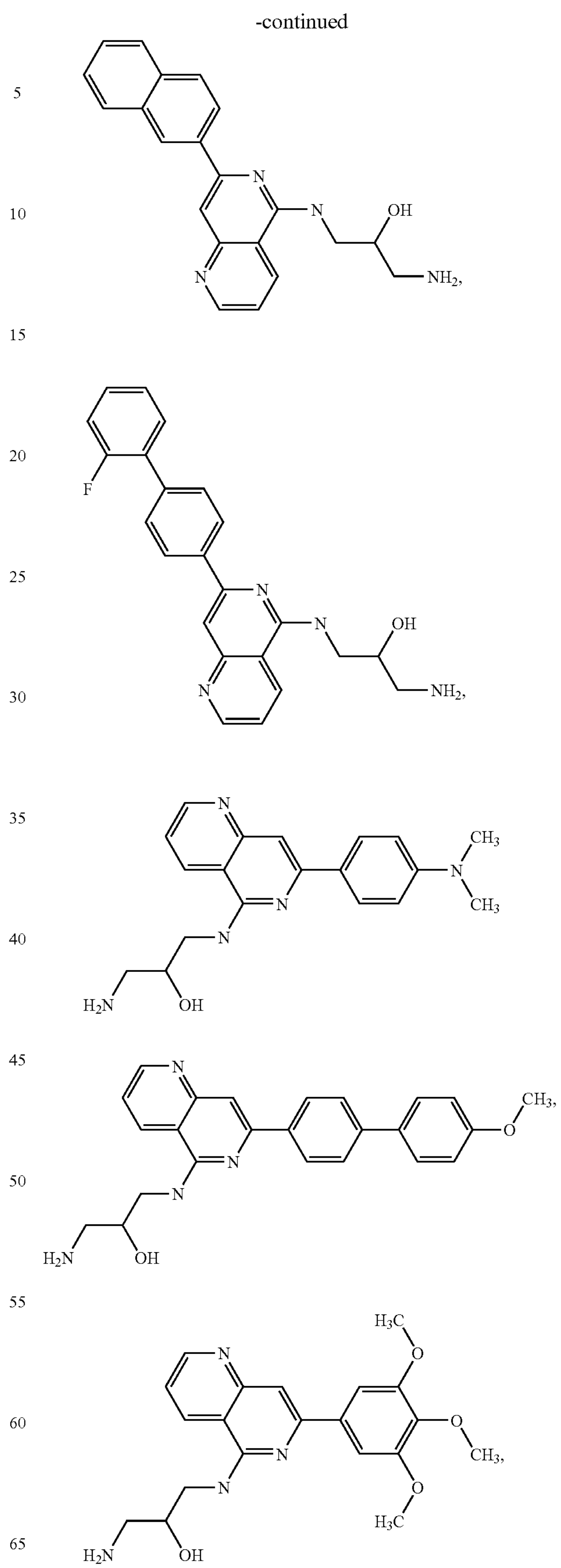

-continued
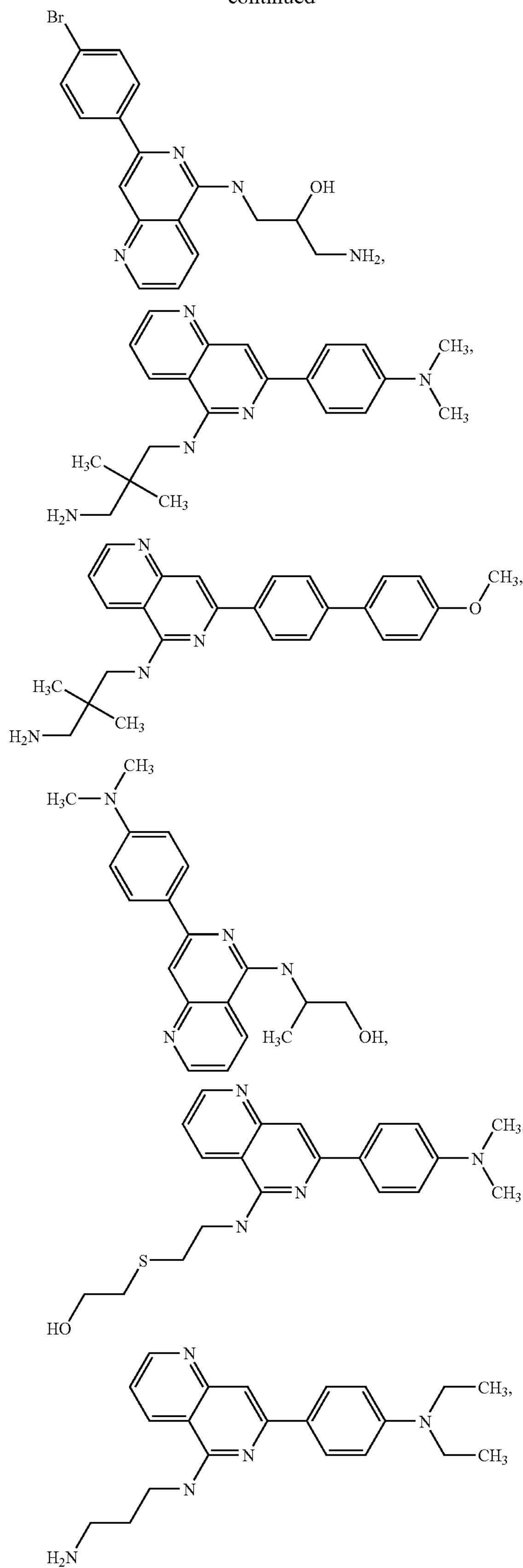
-continued
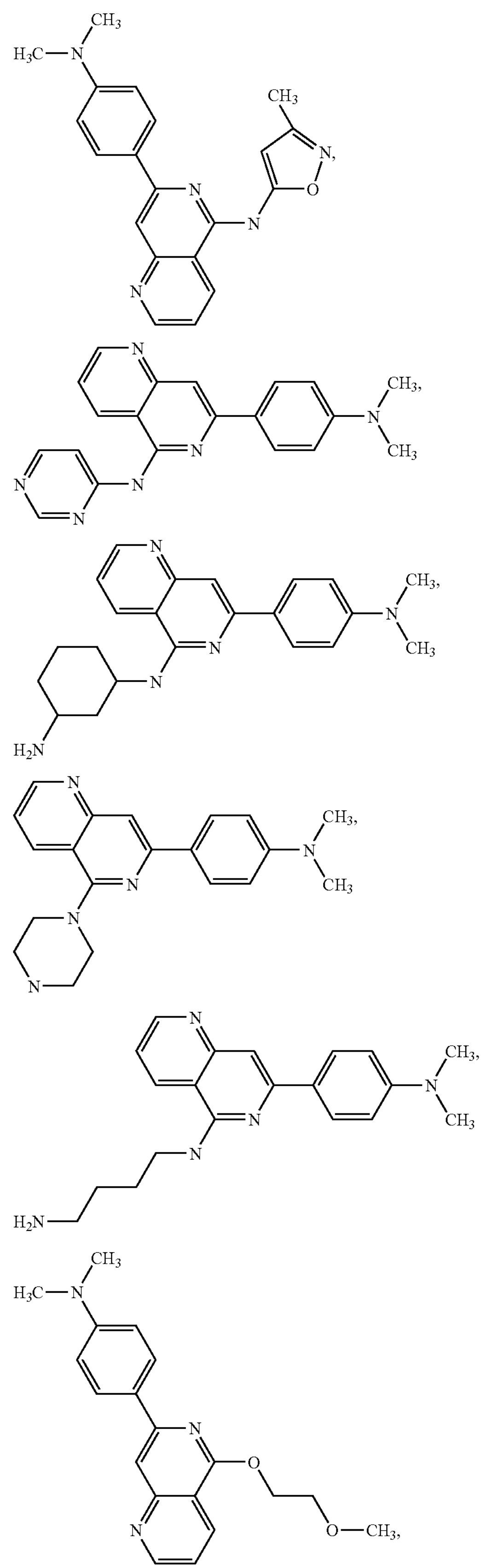

-continued
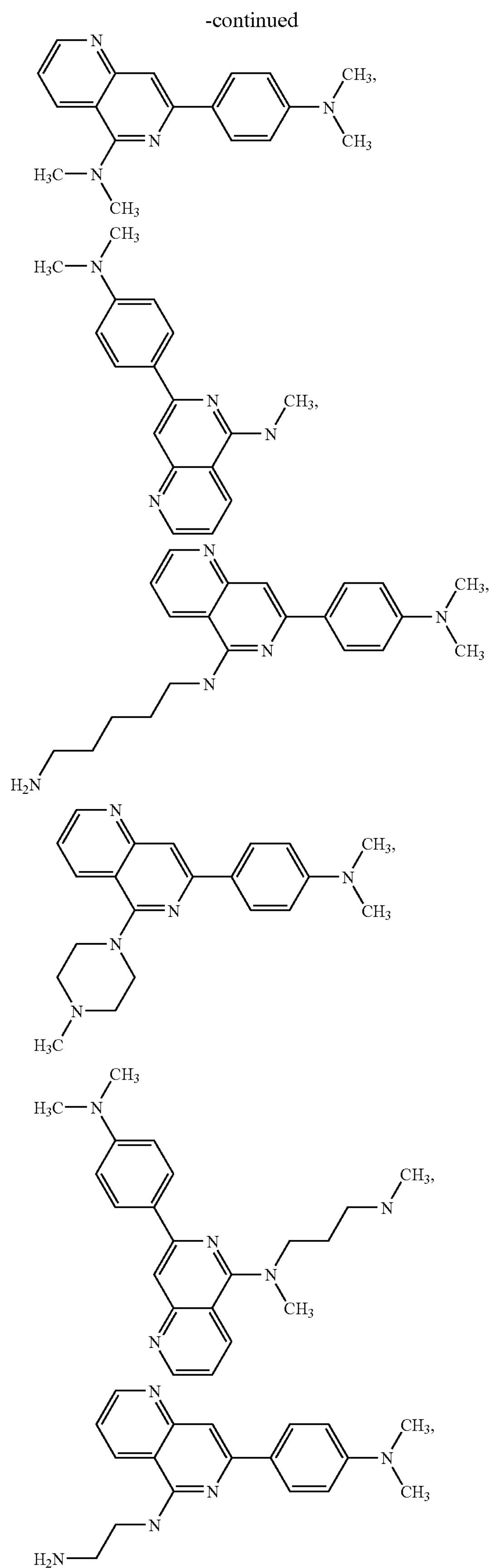
-continued
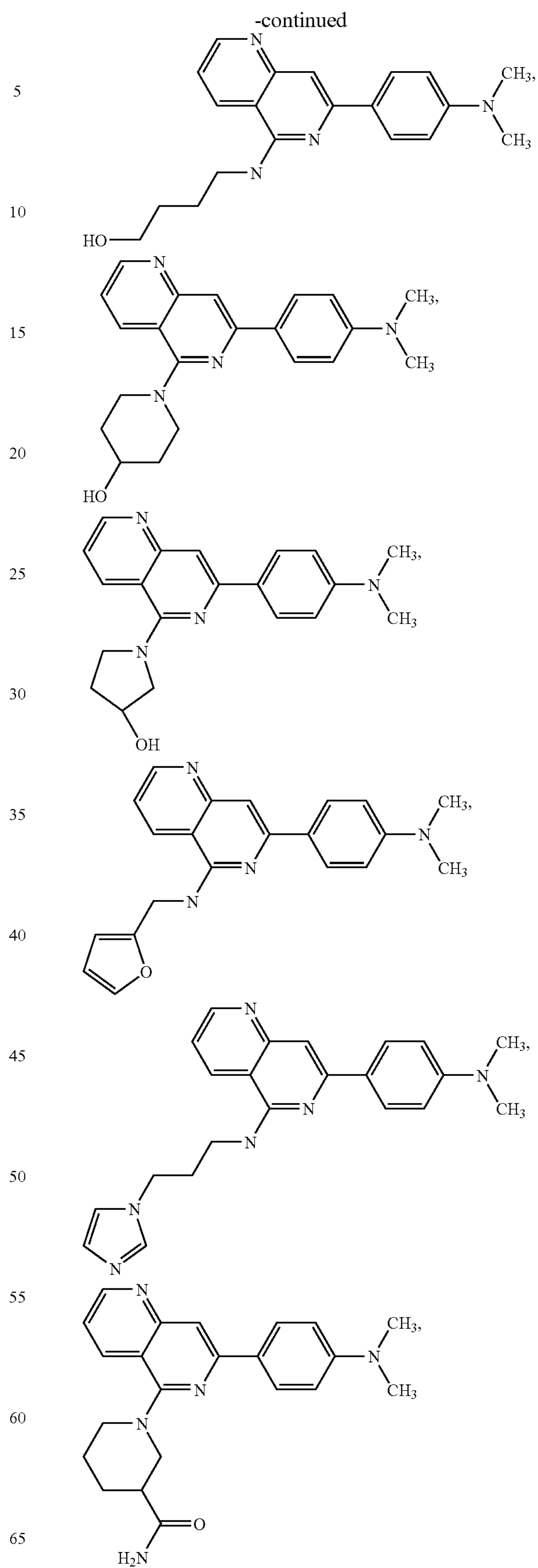

-continued
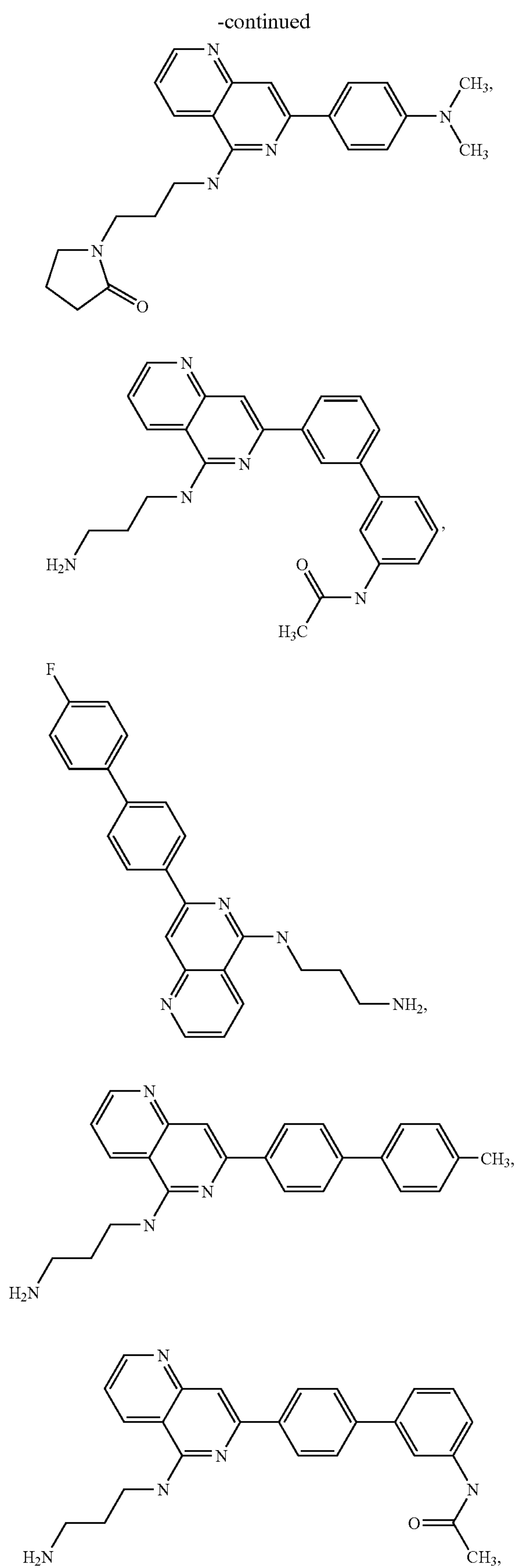
-continued
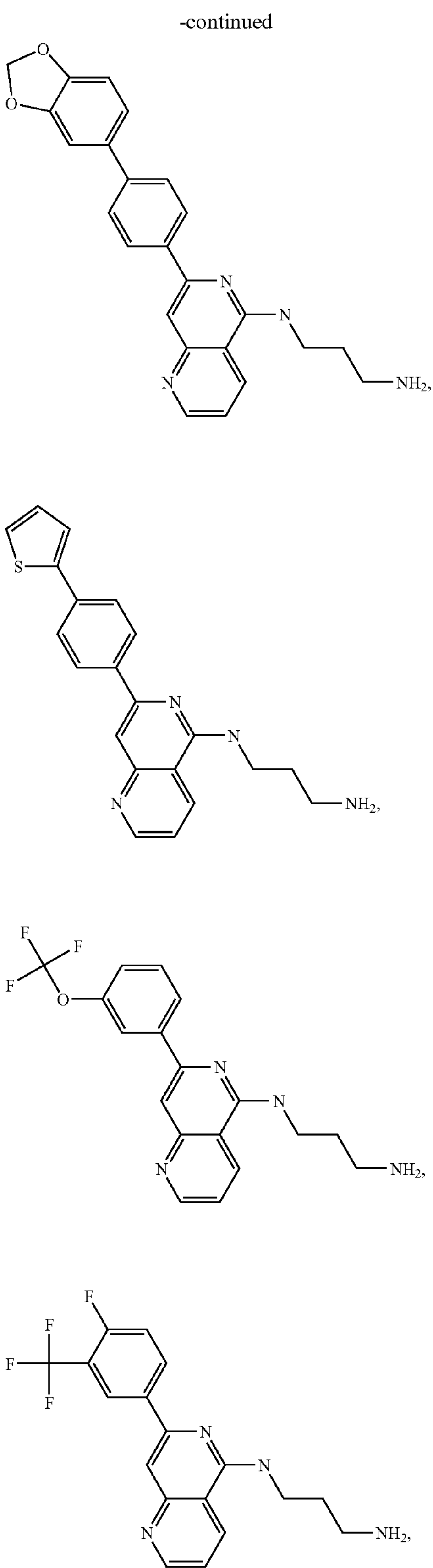

-continued
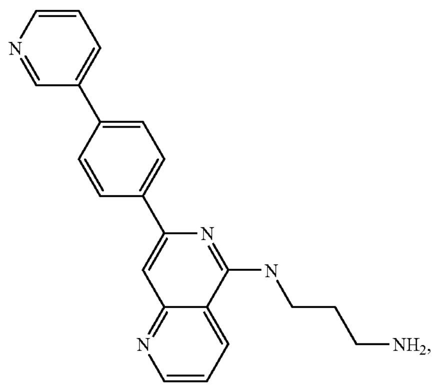
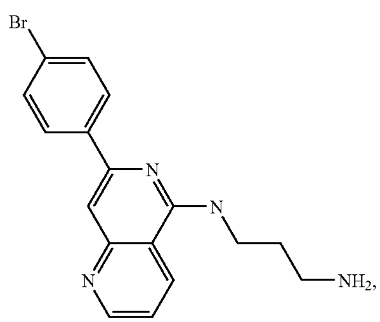
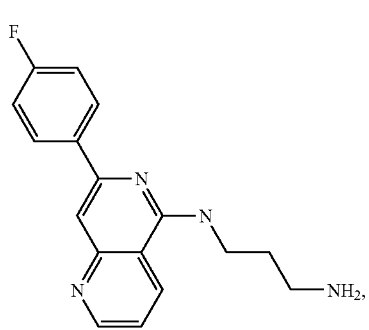
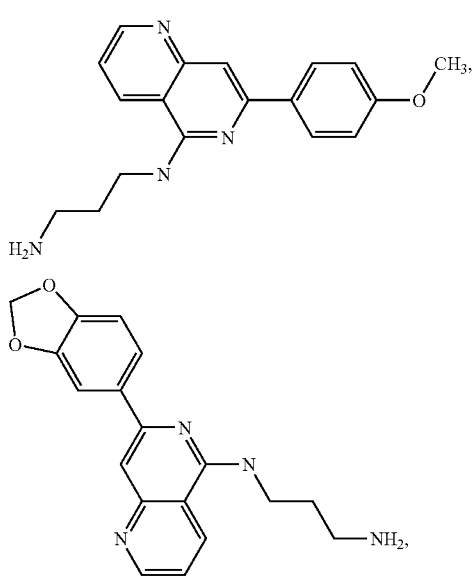
-continued
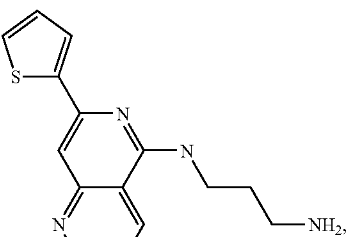
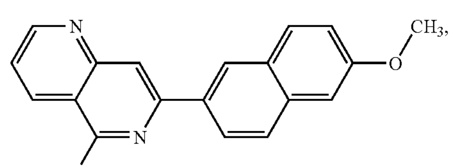
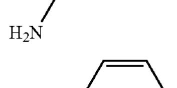
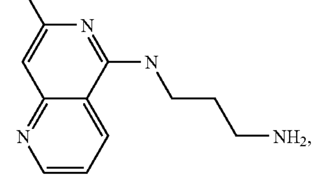
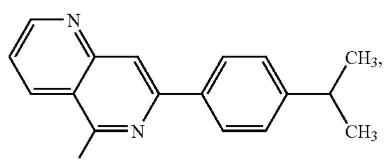
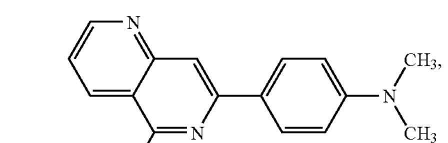
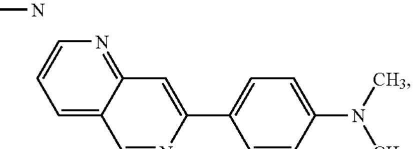

-continued
-continued
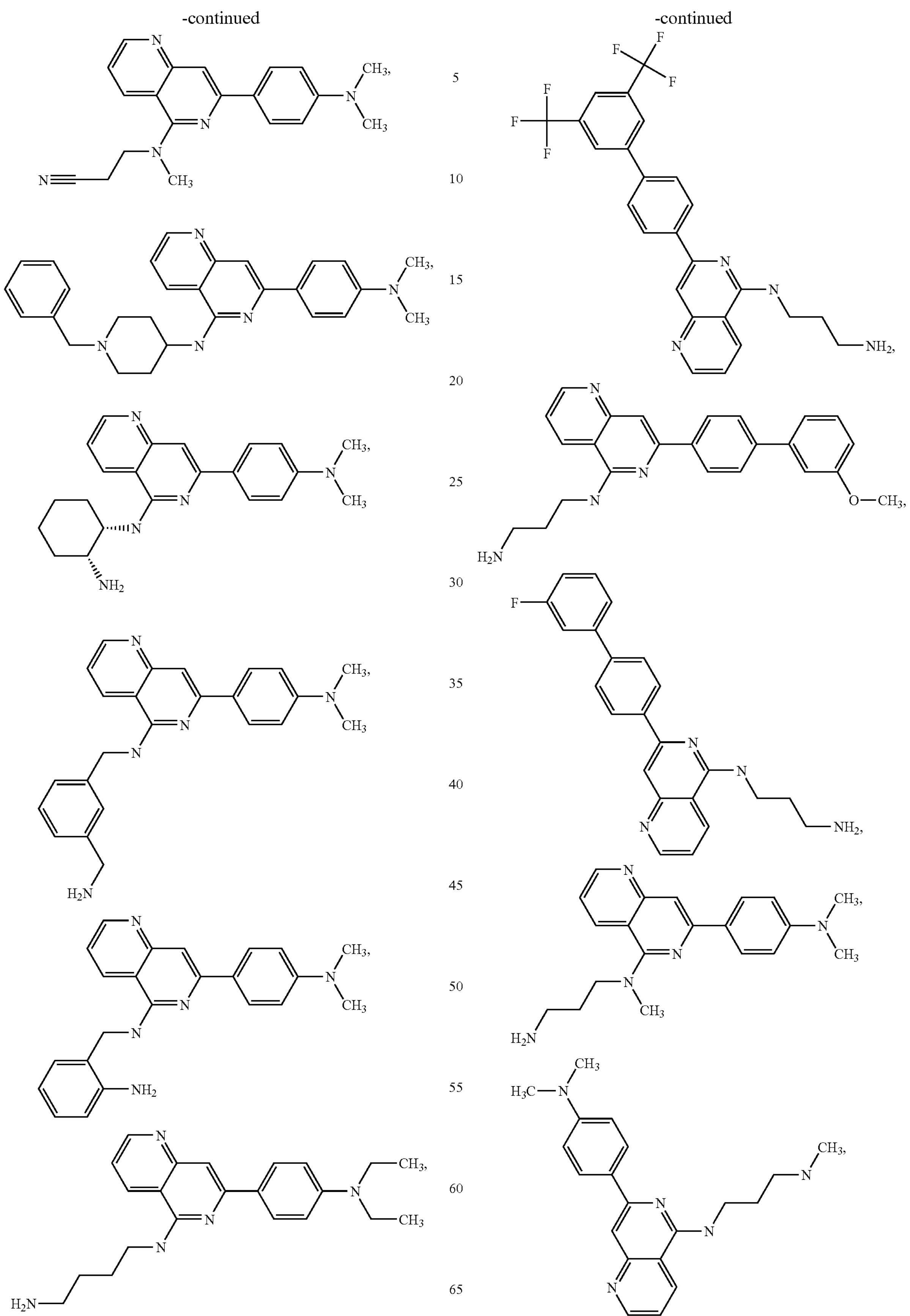

-continued
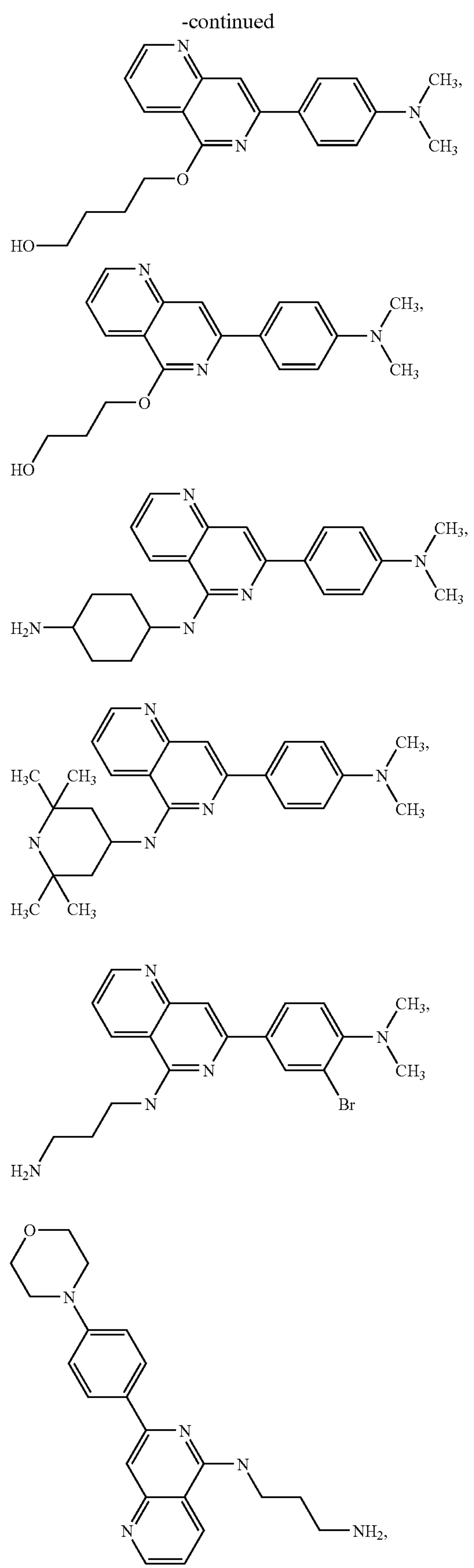
-continued
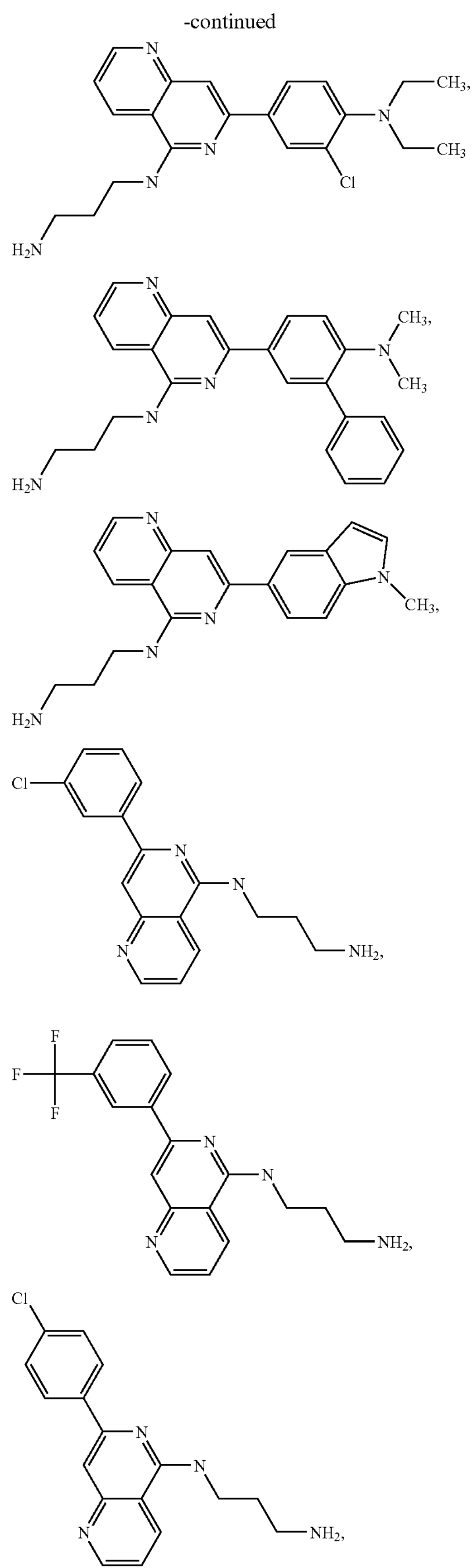

-continued
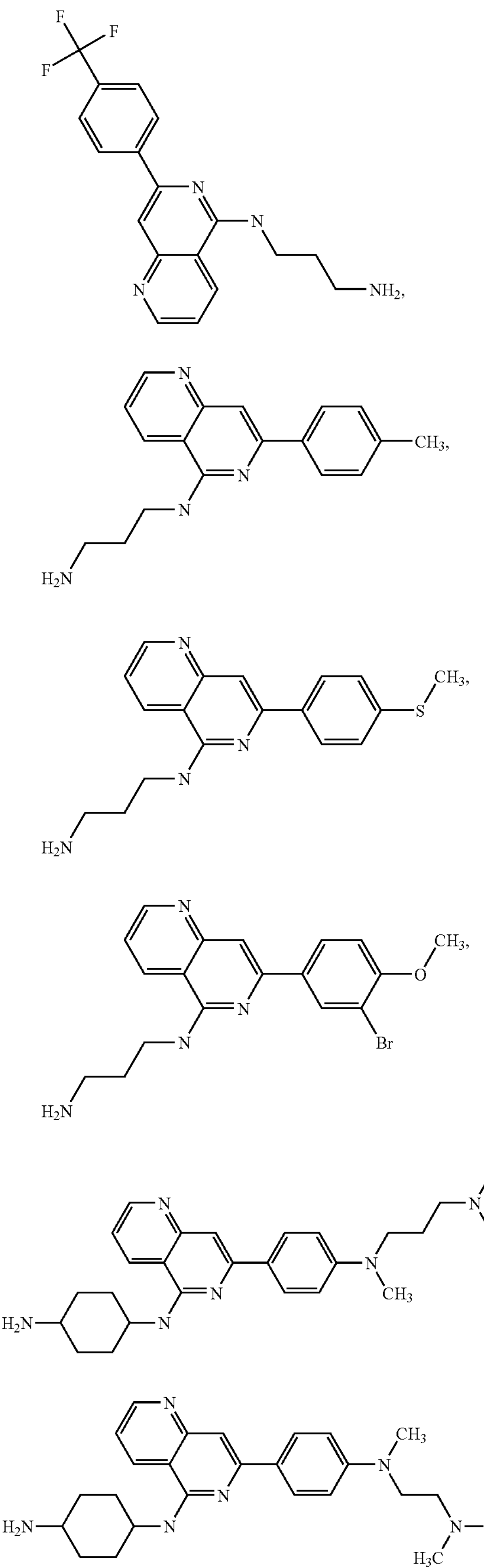
-continued
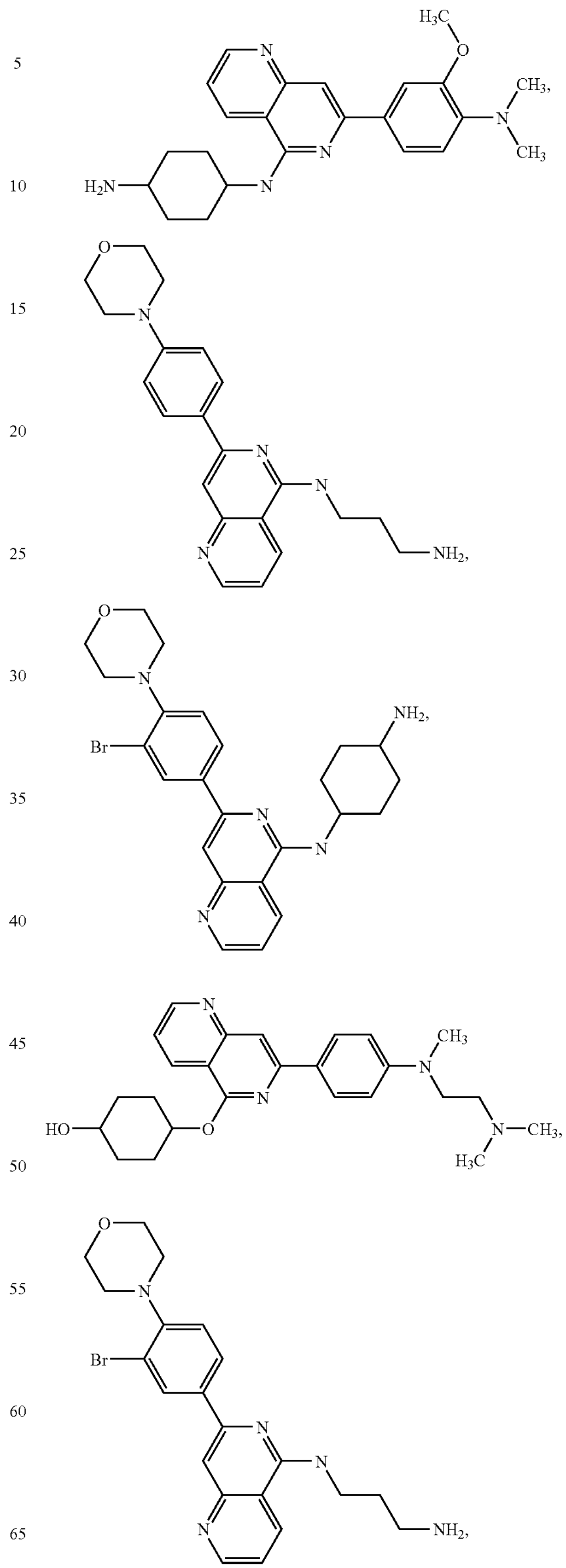

-continued
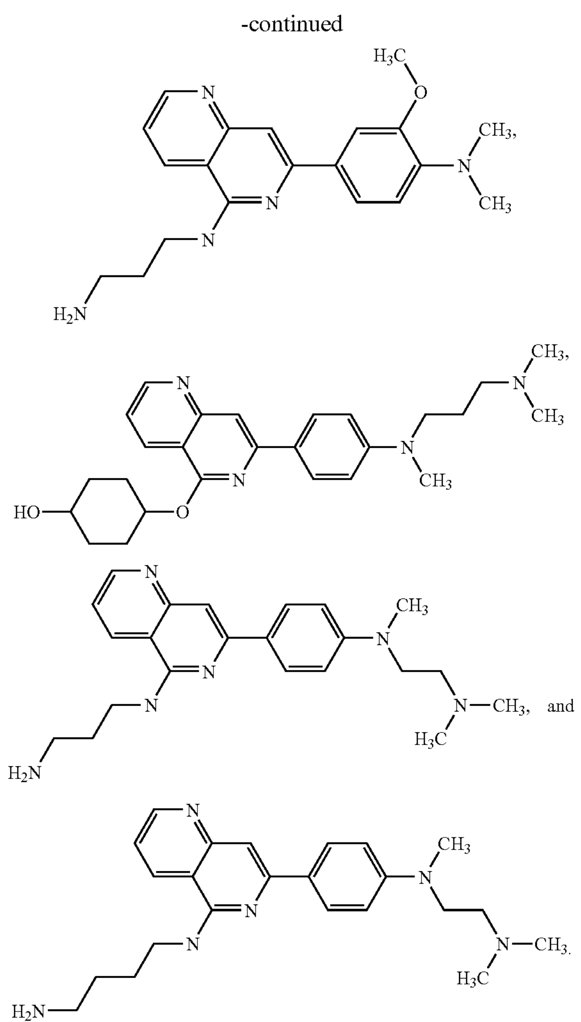
-continued
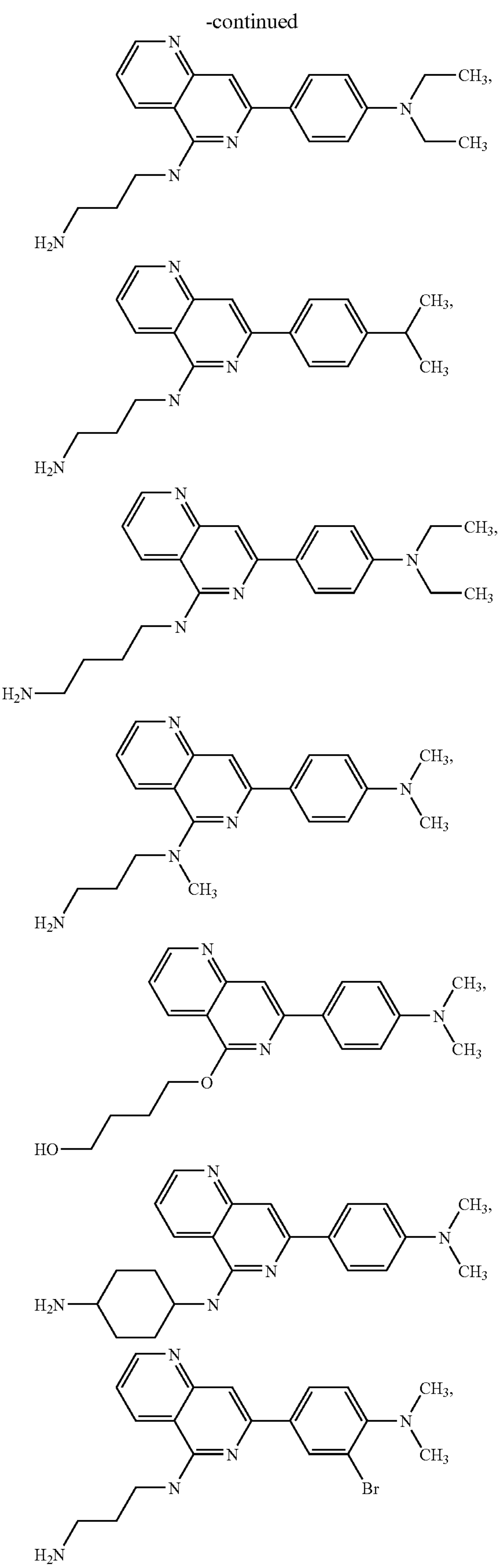
In another embodiment of the invention, there are provided the following compounds:
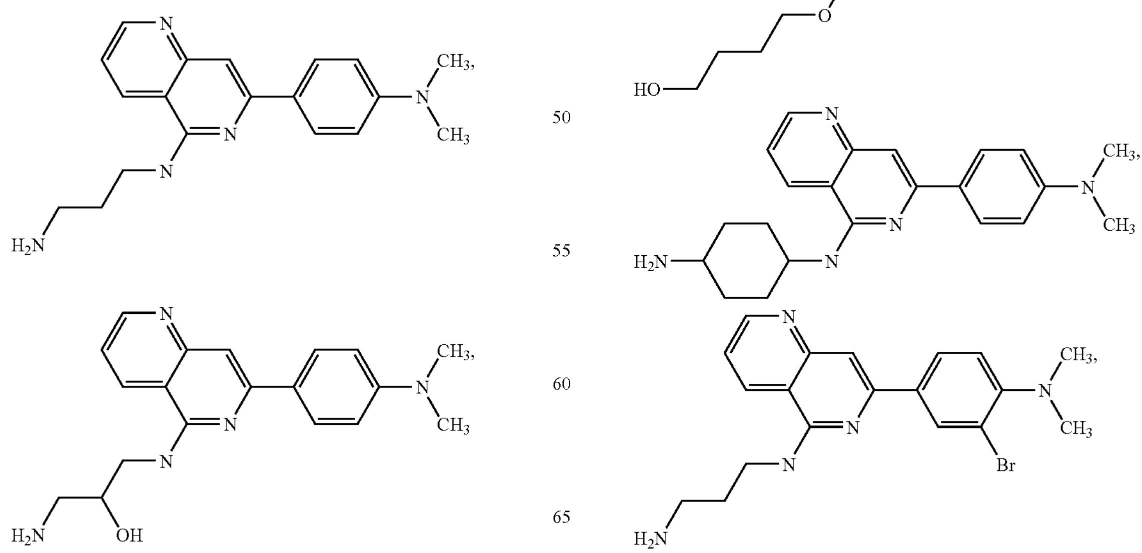

-continued
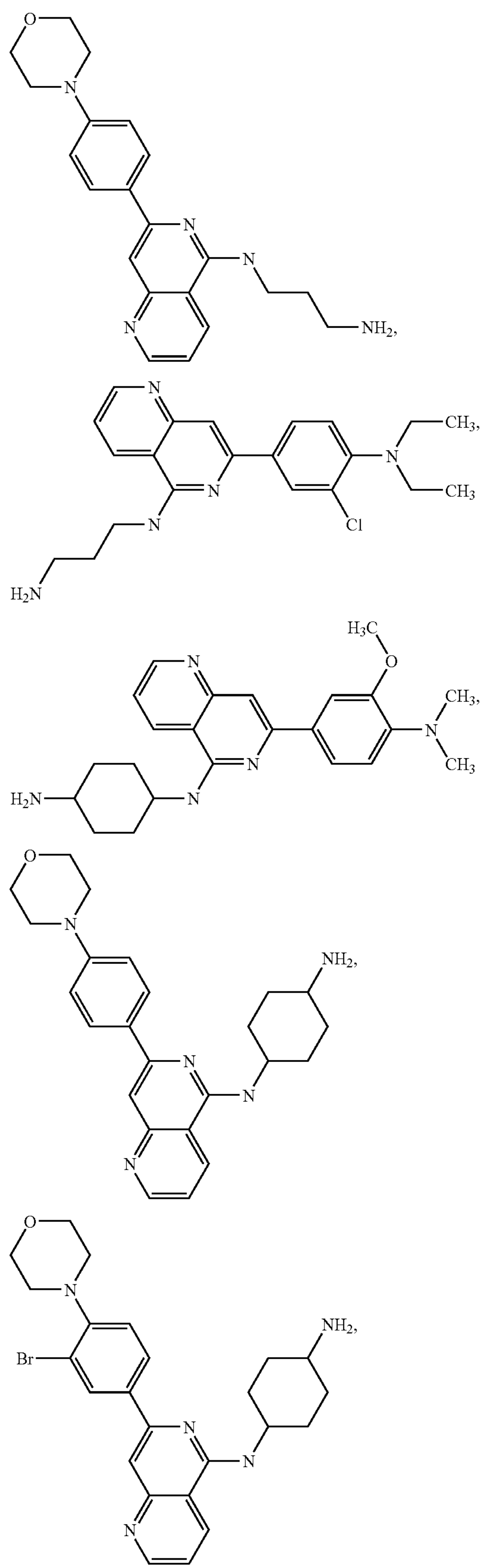
-continued
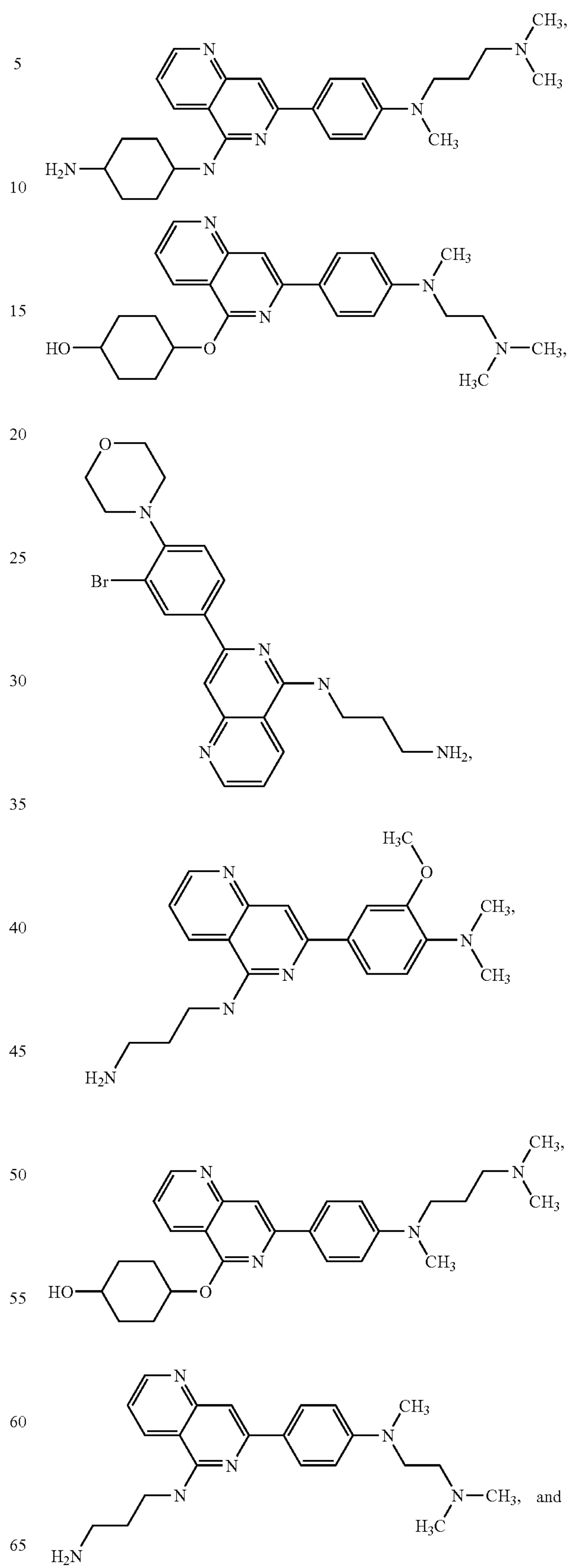

-continued

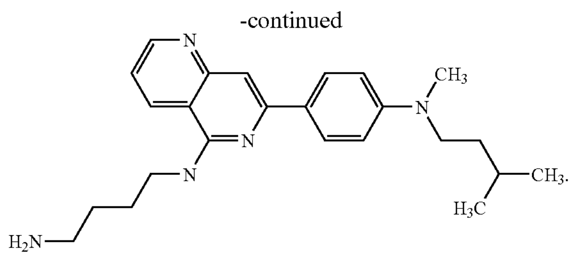

The invention includes pharmaceutically acceptable derivatives of compounds of formula (I). A "pharmaceutically acceptable derivative" refers to any pharmaceutically acceptable acid, salt or ester of a compound of this invention, or any other compound which, upon administration to a patient, is capable of providing (directly or indirectly) a compound of this invention, a pharmacologically active metabolite or pharmacologically active residue thereof.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N-($C_1$-$C_4$ alkyl)$_4^+$ salts.

In addition, the compounds of this invention include prodrugs of compounds of the formula (I). Prodrugs include those compounds that, upon simple transformation, are modified to produce the compounds of the invention. Simple chemical transformations include hydrolysis, oxidation and reduction which occur enzymatically, metabolically or otherwise. Specifically, when a prodrug of this invention is administered to a patient, the prodrug may be transformed into a compound of formula (I), thereby imparting the desired pharmacological effect.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes all such tautomers.

The compounds of the invention are only those which are contemplated to be 'chemically stable' as will be appreciated by those skilled in the art. For example, a compound which would have a 'dangling valency', or a 'carbanion' are not compounds contemplated by the invention.

As used herein, the following abbreviations are used:

BuOH is butanol;

DMF is dimethylformamide;

DMSO is dimethyl sulfoxide

EtOAc is ethyl acetate;

EtOH is ethanol;

HPLC is high-performance liquid chromatography

LDA is lithium diisopropylamide;

MeOH is methanol;

THF is tetrahydrofuran;

TLC is thin layer chromatography

All terms as used herein in this specification, unless otherwise stated, shall be understood in their ordinary meaning as known in the art. For example, "$C_{1-6}$alkoxy" is a $C_{1-6}$alkyl with a terminal oxygen, such as methoxy, ethoxy, propoxy, pentoxy and hexoxy. All alkyl, alkylene or alkynyl groups shall be understood as being branched or unbranched unless otherwise specified. Other more specific definitions are as follows:

The term "alkyl" refers to a saturated aliphatic radical containing from one to ten carbon atoms or a mono- or polyunsaturated aliphatic hydrocarbon radical containing from two to twelve carbon atoms unless otherwise stated. The mono- or polyunsaturated aliphatic hydrocarbon radical contains at least one double or triple bond, respectively. "Alkyl" refers to both branched and unbranched alkyl groups. Examples of "alkyl" include alkyl groups which are straight chain alkyl groups containing from one to eight carbon atoms and branched alkyl groups containing from three to ten carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C═O). Each alkyl or alkyl analog described herein shall be understood to be optionally partially or fully halogenated.

The term "cycloalkyl" refers to the cyclic analog of an alkyl group, as defined above. Examples of cycloalkyl groups are saturated or unsaturated nonaromatic cycloalkyl groups containing from three to eight carbon atoms, and other examples include cycloalkyl groups having three to six carbon atoms.

The term "heterocycloalkyl" refers to a stable 4-8 membered (but preferably, 5 or 6 membered) monocyclic or 8-11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heterocycloalkyl" include radicals such as pyrrolinyl, pyrrolidinyl, pyrazolinyl, pyrazolidinyl, piperidinyl, morpholinyl, thiomorpholinyl, piperazinyl, indolinyl, azetidinyl, tetrahydropyranyl, tetrahydrothiopyranyl, tetrahydrofuranyl, hexahydropyrimidinyl, hexahydropyridazinyl, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione.

The term "halogen" refers to bromine, chlorine, fluorine or iodine.

The term "aryl" shall be understood to mean a 6-12 membered aromatic carbocycle, which can be a single ring or can be multiple rings fused together or linked covalently. The term "aryl" includes, for example, phenyl and naphthyl; other terms comprising "aryl" will have the same definition for the aryl component, examples of these moieties include: arylalkyl, aryloxy or arylthio.

The term "heteroaryl" refers to a stable 5-8 membered (but preferably, 5 or 6 membered) monocyclic or 8-11 membered bicyclic aromatic heterocycle radical. Each heterocycle consists of carbon atoms and from 1 to 4 heteroatoms chosen from nitrogen, oxygen and sulfur. The heteroaryl group may be attached by any atom of the ring which results in the creation of a stable structure. Examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl, As used herein above and throughout this application, "nitrogen" and "sulfur" include any oxidized form of nitrogen and sulfur and the quaternized form of any basic nitrogen.

General Synthetic Methods

The invention additionally provides for methods for making the compounds of the formula (I). The compounds of the invention may be prepared by the general methods and examples presented below, and methods known to those of ordinary skill in the art.

Reaction progress may be monitored by conventional methods such as thin layer chromatography (TLC). Intermediates and products may be purified by methods known in the art, including column chromatography, HPLC or recrystallization.

As illustrated in Scheme I, a 2-methylnicotinic acid derivative (II) is treated with a strong base such as lithium diisopropylamide (LDA) in a suitable solvent such as THF at about −78° C. to 0° C. to form the dianion. This is followed by addition of a nitrile bearing the desired $R_7$, preferably at about −78° C., and allowing the reaction to warm to about room temperature until reaction is complete to provide the [1,6]-naphthyridin-5-ol (III), which may also exist as the tautomeric 6H-[1,6]-naphthyridin-5-one (IIIa).

The [1,6]-naphthyridin-5-ol is then treated with a suitable halogenating agent. For example, treatment with $POCl_3$, optionally in the presence of a suitable base such as N,N-diethylaniline, at a temperature of about 0° C. to 140° C., preferably at about 100° C. to 135° C., provides the 5-chloro-[1,6]-naphthyridine IV. This may then be reacted with an excess of the desired amine ($R'NH_2$) at a suitable temperature, preferably about 100° C. to 140° C., optionally in a sealed reaction vessel, to provide a compound of formula (I) having an amine at $R_5$. If a compound of formula (I) having an ether link at $R_5$ is desired, one may react IV with the desired alcohol (R'OH), in the presence of a suitable base such as sodium hydride in a suitable solvent such as DMF at a temperature of about 0° C. to 100° C., preferably at about room temperature.

Scheme I

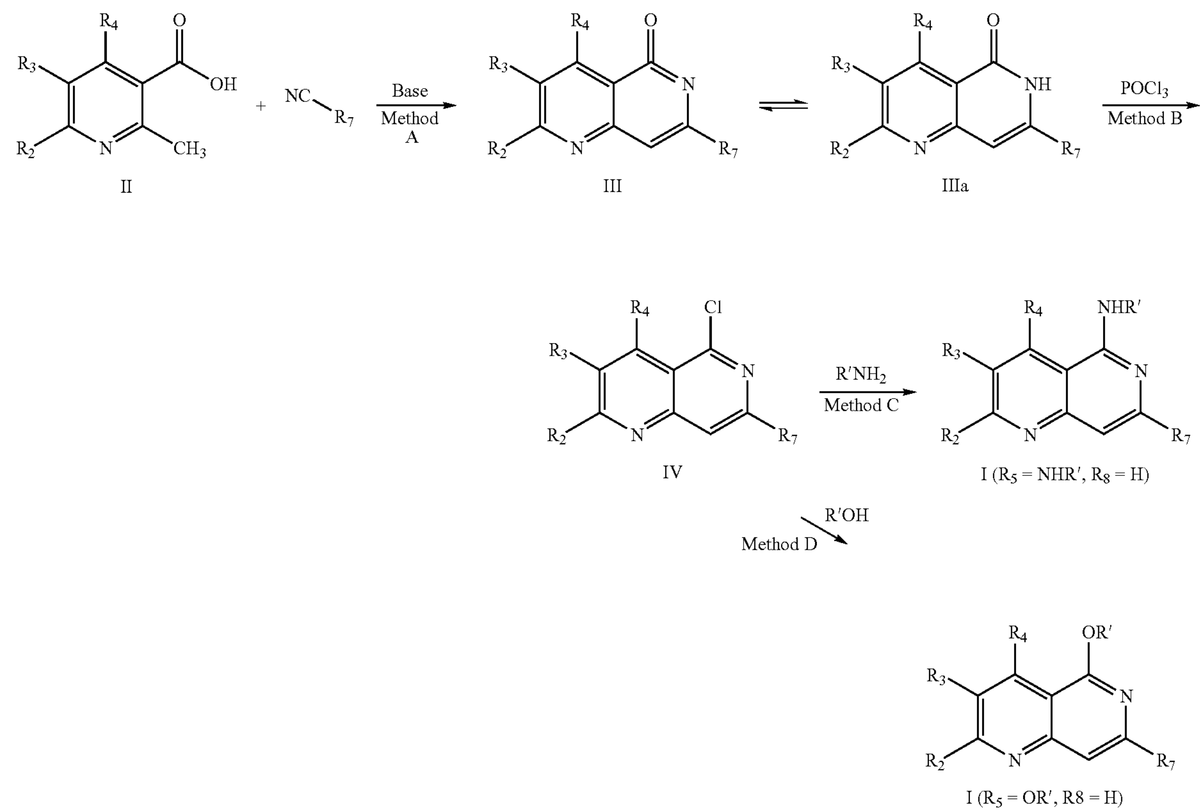

If a compound of formula (I) having $R_8$ being a substituent other than hydrogen is desired, one may react an intermediate of formula (III) with a halogenating agent, preferably N-iodosuccinamide, in a suitable solvent such as DMF, at about room temperature, to provide the 8-iodo intermediate V (Scheme II). The 8-iodo substituent may then be converted to other desired $R_8$ by methods known to those skilled in the art. Likewise, $R_5$ or $R_7$ may be reacted further by methods known to those skilled in the art to prepare additional compounds of formula (I). Several illustrative examples are provided in the Experimental section.

Scheme II

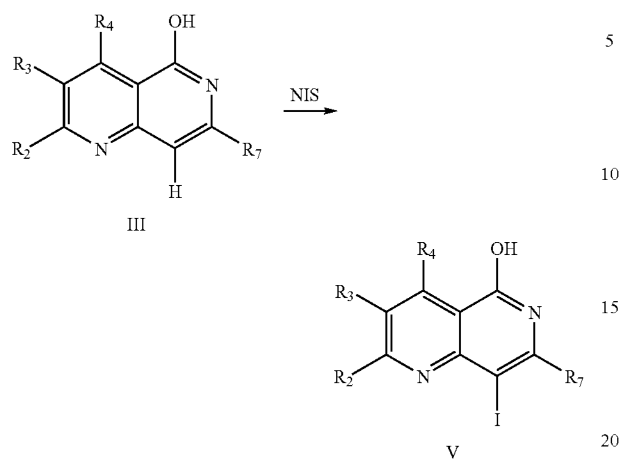

The [1,6]-naphthyridin-5-ol III may also be prepared by an alternative procedure illustrated in Scheme III (Method E).

Scheme III

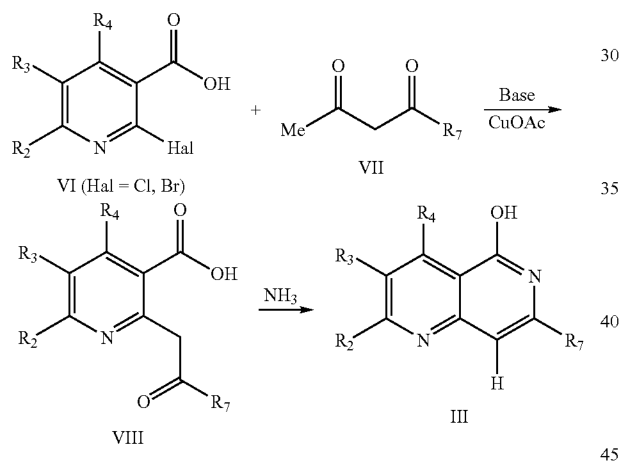

In this procedure, described in the literature (D. E. Ames and W. D. Dodds, J. C. S. Perkin I, 1972, 705), a carbanion is reacted with a 2-halonicotinic acid, preferably a 2-chloro- or 2-bromonicotinic acid, (VI), in the presence of a copper catalyst, preferably copper acetate, to give a 2-(2-substituted-2-oxo-ethyl)nicotinic acid intermediate (VIII). The carbanion may be generated from a 1,3-dicarbonyl compound such as VII, and a base, preferably sodium ethoxide. Subsequent ethanolysis cleaves the acetyl group to provide VIII. Treatment of VIII with ammonia in a suitable solvent, such as dioxane or ethanol, at a suitable temperature, preferably the reflux temperature of the solvent, provides III.

In a variation of Method E illustrated in Scheme IV (Method F), intermediate VIII may be treated with aqueous acid, such as aqueous sulfuric acid, at about room temperature to provide a pyrano[4,3-b]pyridin-5-one (IX). This may then be treated with ammonia in a suitable solvent such as ethanol, at a suitable temperature, preferably about the reflux temperature, to provide III.

Scheme IV

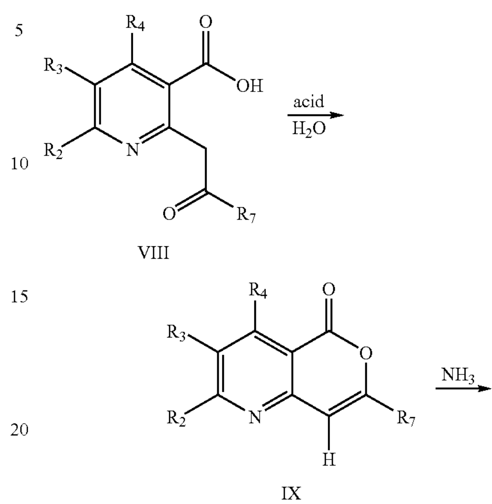

SYNTHETIC EXAMPLES

The following examples are for the purpose of illustrating preferred embodiments of this invention, and are not to be construed as limiting the scope of the invention in any way.

7-Aryl-5-amino-[1,6]naphthyridines may be made by the procedure described in Examples 1-3 below (Methods A-C). By choosing the appropriately substituted aryl nitrile (Example 1) and appropriately substituted amine (Example 3) or alcohol (Example 11) one may obtain the desired compound of formula (I). Alternatively, one may obtain a precursor of the desired compound, which may be further modified synthetically by methods known to those skilled in the art to obtain the desired compound of formula (I).

Example 1

7-(4-Dimethylaminophenyl)-[1,6]naphthyridin-5-ol (Method A)

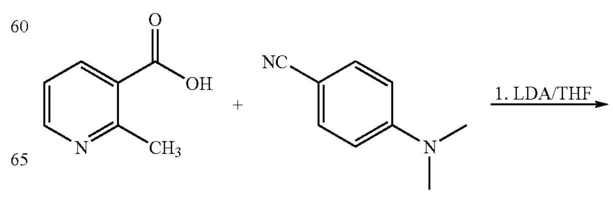

-continued

To a suspension of 2-methylnicotinic acid (1.37 g, 10 mmol) in THF (20 mL), lithium diisopropylamide (2 M solution in THF, 12.5 mL, 25 mmol) was added dropwise at −78° C. The resulting mixture was stirred at −78° C. for 30 minutes then slowly warmed up to 0° C. over 1.5 hours. The mixture was cooled to −78 ° C. and a solution of 4-dimethylaminophenylnitrile (2.19 g, 15 mmol) in THF (10 mL) was added dropwise. The mixture was slowly warmed to room temperature and stirred for 16 hours. Water (20 mL) was added and the THF was removed in vacuo. EtOAc (10 mL) was added and the solution was allowed to stand for two hours. The precipitated solid was collected by filtration to afford the title compound as a yellow solid (1.2 g). $^{1}$H NMR ($CDCl_3$, 400 MHz) δ 11.58 (b, 1H), 8.86 (dd, 1H), 8.45 (d, 1H), 6.86 (d, 1H), 3.92 (s, 3H), 3.88 (s, 3H), 2.87 (s, 6H), MS (m/e) calculated for $C_{15}H_{15}N_3O$ 265, found 266.2 (M+H).

Example 2

5-Chloro-7-(4-dimethylaminophenyl)-[1,6]naphthyridine (Method B)

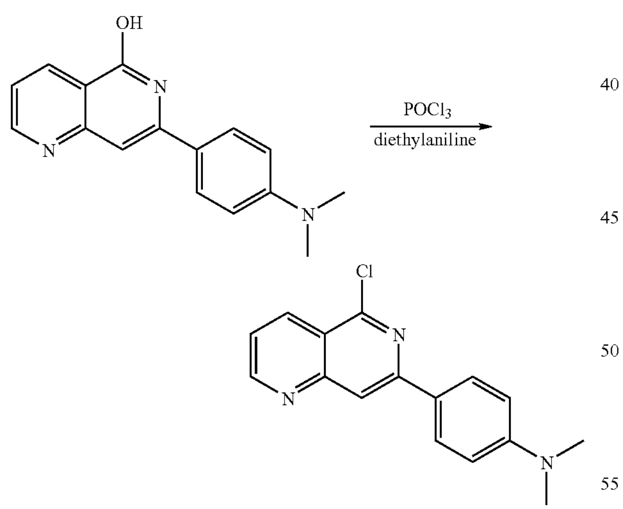

A mixture of 7-(4-dimethylaminophenyl)-[1,6]naphthyridin-5-ol (Example 1) (1.2 g, 5 mmol), $POCl_3$ (10 mL) and N,N-diethylaniline (0.15 g, 1.0 mmol) were stirred at 110° C. for 16 hours. The contents were cooled to room temperature and excess $POCl_3$ was removed in vacuo. The residue was quenched with water and neutralized with aqueous sodium carbonate. The aqueous solution was then extracted with dichloromethane (2×30 mL). The combined organic extracts were dried over anhydrous magnesium sulfate and concentrated in vacuo to give a tan oil. Purification by flash chromatography eluting with hexanes/EtOAc (1:1) afforded the title compound as a yellowish solid (1.1 g). $^{1}$H NMR ($CDCl_3$, 400 MHz) δ 9.03 (dd, 1H), 8.54 (d, 1H), 8.13 (s, 1H), 8.08 (d, 2H), 7.46 (dd, 1H), 6.81 (d, 2H), 3.05 (s, 6H).

Example 3

5-(3-Aminopropylamino)-7-(4-dimethylaminophenyl)-[1,6]naphthyridine (Method C)

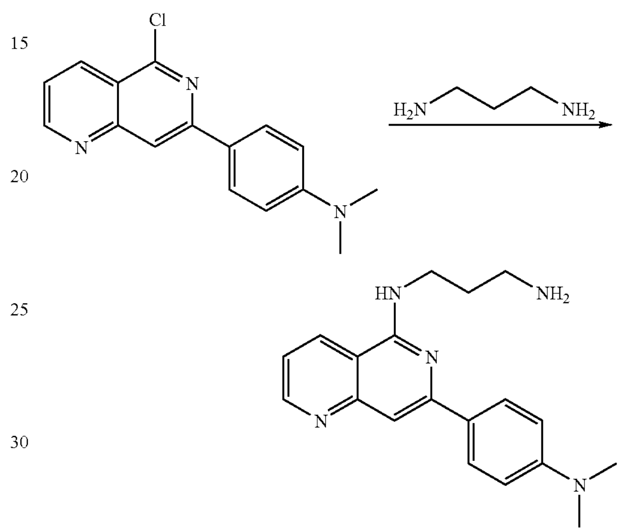

A mixture of 5-chloro-7-(4-dimethylaminophenyl)-[1,6] naphthyridine (Example 2) (10 mg, 0.035 mmol) and 1,3-diaminopropane (200 microL, 2.4 mmol) was stirred at 100 ° C. for 5 hours. After cooling to room temperature, water was added and the resulting mixture was extracted with dichloromethane (2×3 mL). Purification by preparative thin layer chromatography afforded the title compound as a yellow film (8.5 mg). $^{1}$H NMR ($CDCl_3$, 400 MHz) δ 8.85 (dd, 1H), 8.10 (d, 2H), 8.07 (d, 1H), 7.50 (s, 1H), 7.21 (dd, 1H), 6.81 (d, 2H), 3.87 (t, 2H), 3.02 (s, 6H), 2.97 (t, 2H), 1.90 (quint, 2H); MS (m/e) calculated for $C_{19}H_{23}N_5$ 321.2, found 322.4 (M+H).

Examples 4-13 are illustrative of procedures that may be used to modify intermediates to obtain desired compounds of the invention.

Example 4

5-Chloro-7-(3-hydroxyphenyl)-[1,6]naphthyridine

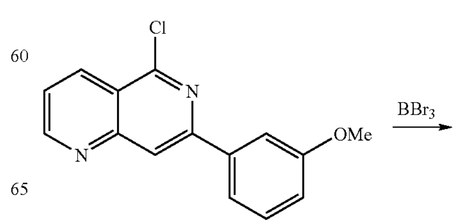

-continued

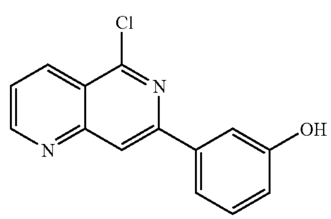

To a solution of 5-chloro-7-(3-methoxyphenyl)-[1,6]naphthyridine (0.052 g, 0.2 mmol) in dichloromethane (2 mL) was added boron tribromide (1 M solution in dichloromethane, 0.4 mL, 0.4 mmol) at −78° C. The resulting mixture was slowly warmed to room temperature. The residue was quenched with water and neutralized with aqueous sodium carbonate. The aqueous solution was then extracted with dichloromethane (2×30 mL). The combined organic extracts were dried over anhydrous magnesium sulfate and concentrated in vacuo to give a tan oil. Purification by flash chromatography eluting with hexanes/EtOAc (1:1) afforded the title compound as a yellowish solid (0.040 g). $^1$H NMR (DMSO-d6, 400 MHz) δ 9.70 (b, 1H), 9.19 (dd, 1H), 8.54-8.64 (m, 1H), 8.37 (s, 1H), 7.77(dd, 1H), 7.64 (m, 2H), 7.32 (t, 1H), 6.87 (m, 1H); MS (m/e) calculated for $C_{16}H_{13}ClN_2O$ 256, found 257.5 (M+H).

Example 5

7-(4'-Methoxybiphenyl-4-yl)-[1,6]naphthyridin-5-ol

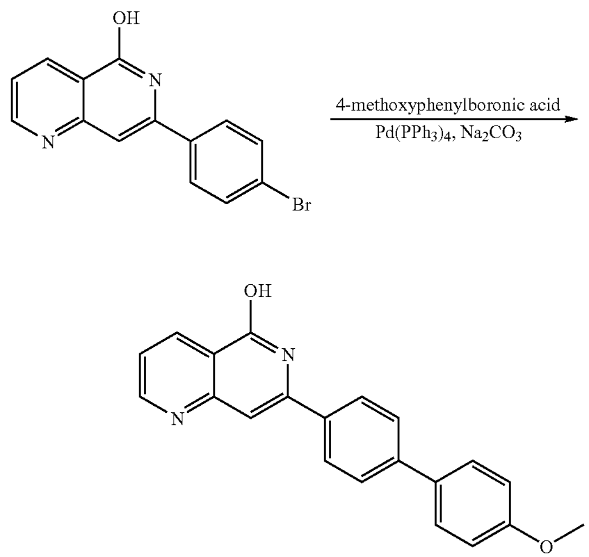

To a suspension of 7-(4-bromophenyl)-[1,6]-naphthyridin-5-ol (0.135 g, 0.45 mmol)) in DMF (4 mL), was added tetrakis (triphenylphosphine)palladium (0.025 g, 0.02 mmol). After 15 minutes, 4-methoxyphenylboronic acid (0.090 g, 0.60 mmol) and sodium carbonate (2 M aqueous solution, 0.5 mL, 1 mmol) was added. The mixture was heated to 100° C. for 12 hours and then cooled to room temperature. The white solid was collected by filtration and washed with water to afford the title compound (0.110 g).

Example 6

5-(3-Aminopropylamino)-7-[6-dimethylamino-biphenyl-3-yl)-[1,6]naphthyridine

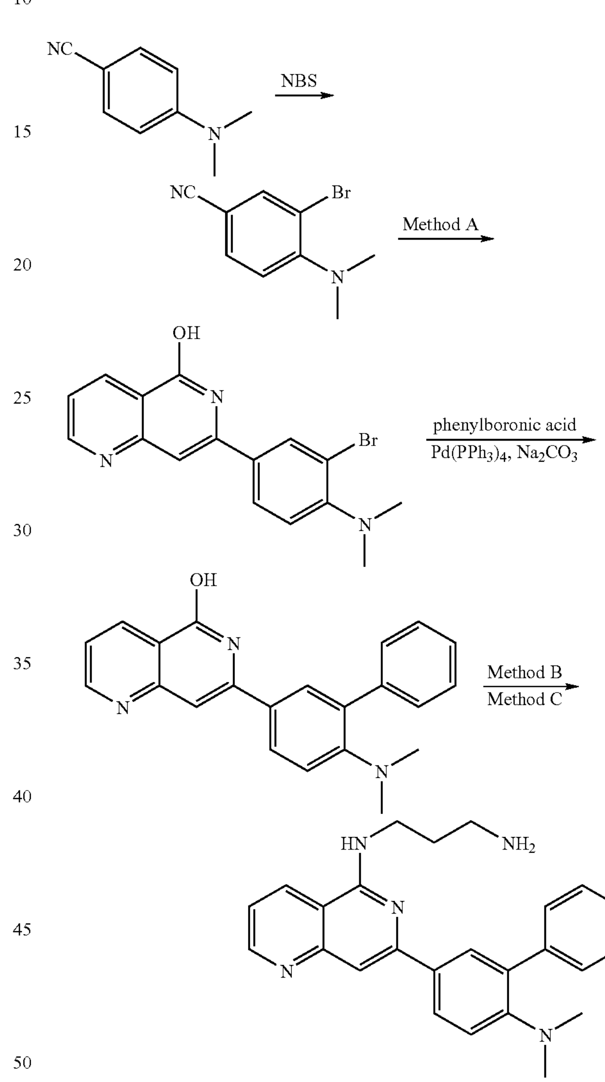

A mixture of 4-dimethylaminobenzonitrile (2.92 g, 20 mmol) and N-bromosuccinmide (3.56 g, 20 mmol) in dichloromethane (50 mL) was stirred at room temperature overnight. The solution was washed with water (20 mL), dried over magnesium sulfate and concentrated to afford 3-bromo-4-dimethylaminobenzonitrile as a white solid (4.27 g).

Treatment of the above intermediate with 2-methylnicotinic acid according to Method A (Example 1) provided the corresponding [1,6]napthyridin-5-ol. Treatment of this with phenylboronic acid using the procedure described in Example 5 provided 7-(6-dimethylamino-biphenyl-3-yl)-[1,6]naphthyridin-5-ol. Conversion to the 5-chloro intermediate using Method B, followed by treatment of this with 1,3-diaminopropane by the procedure described in Method C (Example 3) provided the title compound. $^1$H NMR ($CDCl_3$, 400 MHz) δ 8.82 (dd, 1H), 8.16 (d, 1H), 8.04 (dd, 1H), 8.00 (d, 1H), 7.63 (dd, 2H), 7.52 (s, 1H), 7.41 (t, 2H), 7.29 (t, 1H), 7.19 (dd, 1H), 7.08 (d, 1H), 3.84 (t, 2H), 3.00 (t, 2H), 2.58 (s, 6H), 1.99 (t, 2H); MS (m/e) calculated for $C_{25}H_{27}N_5$ 397, found 398.3 (M+H).

Example 7

5-(3-Aminopropylamino)-7-(3-chloro-4-diethylaminophenyl)-[1,6]naphthyridine

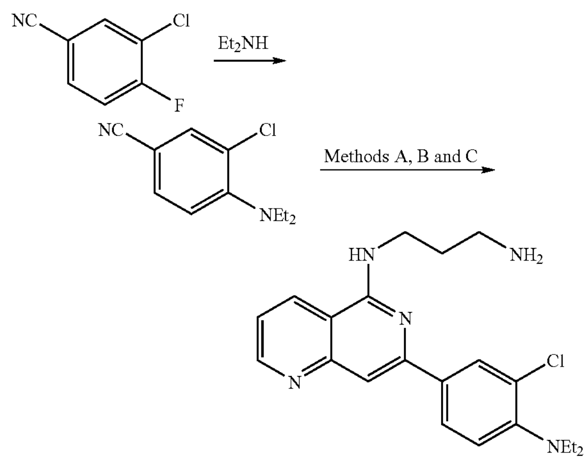

A sealed tube with 3-chloro-4-fluorobenzonitrile (0.366 g, 2.4 mmol) and diethylamine (0.6 mL, 5.8 mmol) was heated to 100° C. for 8 hours. The reaction was allowed to cool to room temperature and water (5 mL) was added. The solution was extracted with dichloromethane (2×5 mL), dried over magnesium sulfate and concentrated in vacuo to afford 3-chloro-4-diethylaminobenzonitrile as an oil (0.38 g). This was reacted as described in Methods A-C (Examples 1-3) to provide the title compound. $^1$H NMR ($CDCl_3$, 400 MHz) δ 8.89 (dd, 1H), 8.26 (d, 1H), 8.11 (ddd, 1H), 7.97 (dd, 2.2 Hz, 1H), 7.53 (d, 1H), 7.27 (dd, 1H), 7.15 (d, 1H), 3.86 (b, 2H), 3.20 (q, 4H), 3.03 (t, 2H), 1.91 (quint, 2H), 1.08 (t, 6H); MS (m/e) calculated for $C_{21}H_{26}ClN_5$ 383, found 384.3 (M+H).

Example 8

5-(3-Aminopropylamino)-7-(3-methoxy-4-dimethylaminophenyl)-[1,6]naphthyridine

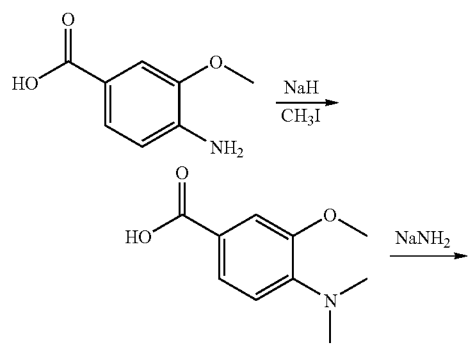

-continued

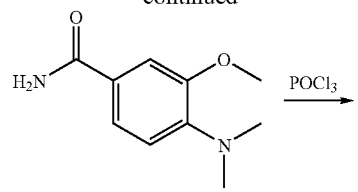

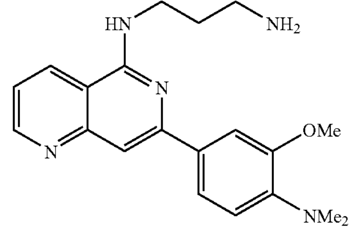

To a solution of 3-methoxy-4-aminobenzoic acid (1.5 g, 9 mmol) in DMF (10 mL) was added sodium hydride (60% in mineral oil, 1.5 g, 37.5 mmol) at 0° C. in portions. After stirring for 30 minutes, methyl iodide (6 g, 45 mmol) was added. The mixture was stirred overnight and quenched by addition of water. The aqueous mixture was extracted with dichloromethane (2×20 mL), dried over sodium sulfate and concentrated in vacuo. Purification by flash chromatography eluting with hexane/EtOAc (4:1) afforded 3-methoxy-4-dimethylaminobenzoic acid as an oil (1.8 g).

A suspension of the above intermediate (1.20 g, 5.7 mmol) and sodium amide (1.0 g, 25 mmol) in toluene (20 mL) was heated to 108° C. for 16 hours. The solution was allowed to cool to room temperature, water was added dropwise, and the resulting mixture was extracted with EtOAc (2×20 mL). The combined organic extracts were dried over sodium sulfate and concentrated in vacuo. Purification by flash chromatography eluting with hexane and EtOAc (1:1) afforded 3-methoxy-4-dimethylaminobenzamide as an oil (0.35 g).

A mixture of the above benzamide (0.220 g, 1.25 mmol), $POCl_3$ (1 mL) and diisopropylethylamine (0.5 mL) was heated to 105° C. for 16 hours and then cooled to room temperature. The solution was poured into ice water and neutralized with sodium carbonate, then extracted with EtOAc (2×20 mL). The combined organic extracts were dried over sodium sulfate and concentrated in vacuo. Purification by flash chromatography eluting with hexanes/EtOAc (2:1) afforded 3-methoxy-4-dimethylaminobenzonitrile as an oil (0.20 g).

The above benzonitrile was reacted as described in Methods A-C (Examples 1-3) to provide the title compound. $^1$H NMR ($CD_3OD$) δ 8.88 (b, 1H), 8.13 (d, 1H), 7.74-7.77 (m, 2H), 7.56 (s, 1H), 7.21 (dd, 1H), 7.08 (b, 1H), 7.02 (d, 1H), 4.00 (s, 3H), 3.88 (b, 2H), 2.85 (s, 6H), 1.96 (b, 2H); MS (m/e) calculated for $C_{20}H_{25}N_5O$ 351, found 352 (M+H).

Example 9

5-(3-Aminopropylamino)-7-(4-diethylaminophenyl)-3-methyl-[1,6]naphthyridine

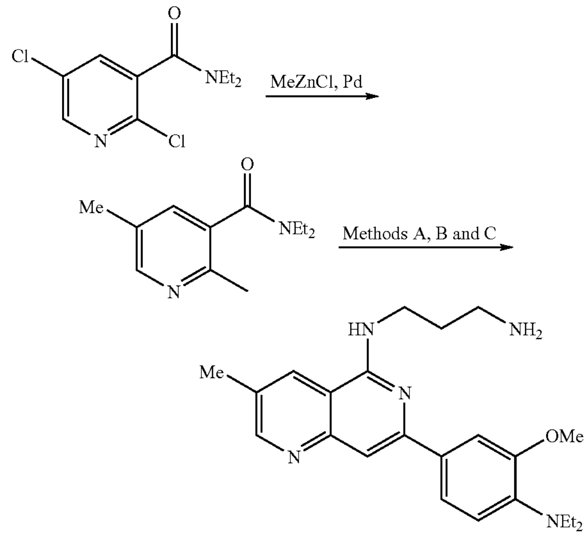

To a solution of N,N-diethyl-2,5-dichloronicotinamide (0.984 g, 4.0 mmol) in THF (15 mL) was added palladium acetate (12 mg, 0.05 mmol) and 2-(di-t-butylphosphino)biphenyl (28 mg, 0.09 mmol). After the mixture was stirred for 5 minutes, methylzinc chloride (2 M solution in dichloromethane, 4.5 mL, 9 mmol) was added. The contents were stirred at room temperature for 14 hours. Water was added and THF was removed in vacuo. The solution was extracted with EtOAc (2×20 mL) and the combined organic extracts were dried over sodium sulfate and concentrated in vacuo. Purification by flash chromatography eluting with hexanes/EtOAc (1:1) afforded N,N-diethyl-2,5-dimethylnicotinamide as an oil (0.31 g).

The above diethylamide was reacted with 4-diethylaminobenzonitrile under conditions described in Method A (Example 1) and the resulting intermediate reacted as described in Methods B and C (Examples 2 and 3) to provide the title compound. $^1$H NMR ($CDCl_3$, 400 MHz) δ 8.85 (d, 1H), 7.29 (d, 1H), 3.65 (b, 2H), 3.13 (q, 2H), 2.47 (s, 3H), 2.31 (s, 3H), 1.27 (t, 3H), 1.05 (t, 3H); MS (m/e) calculated for $C_{12}H_{18}N_2O$ 206, found 207 (M+H).

Example 10

5-(3-Aminopropylamino-7-(3'-fluorobiphenyl-3-yl)-[1,6]-naphthyridine

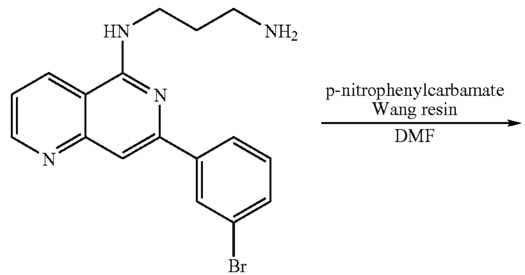

-continued

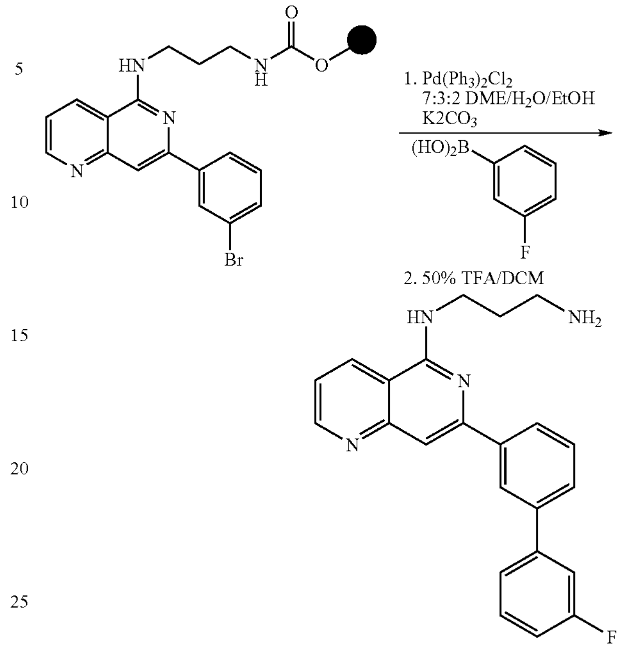

This example is representative of a procedure using a Suzuki reaction carried out on a resin-bound intermediate. This procedure may be used to prepare compounds with a substituted biphenyl in the 7-position.

A suspension of 5-(3-aminopropylamino)-7-(3-bromophenyl)-6H-[1,6]naphthyridine (250 mg, 0.69 mmol) and p-nitrophenylcarbamate Wang resin (500 mg, 0.93 mmol/g loading, 0.47 mmol) in DMF (5 mL) was stirred overnight at room temperature. The suspension was filtered and the resin was washed successively three times with DMF, MeOH, and dichloromethane, then dried under vacuum overnight to afford resin bound compound.

The resin-bound compound above (50 mg, 0.0465 mmol), dichloro(bis-triphenylphosphine) palladium (3 mg, 0.0042 mmol), potassium carbonate (50 μl of a 400 mg/mL solution in water) and 3-fluorophenylboronic acid (64 mg, 0.232 mmol) were suspended in a 7:3:2 mixture of dimethoxyethane/water/EtOH and allowed to heat to 140° C. for 30 minutes in a Smith Synthesizer microwave apparatus from Personal Chemistry. The reaction was filtered and washed three times successively with DMF, MeOH, and dichloromethane. The resin was then dried overnight under vacuum and product was cleaved from the resin using 50% trifluoroacetic acid/dichloromethane (1 mL). The resin was filtered, washed once with 50% trifluoroacetic acid/dichloromethane (1 mL), and the filtrate concentrated to dryness in vacuo to afford the title compound as a film (8 mg). MS (m/e) calculated for $C_{23}H_{21}FN_4$ 372.17, found 373.2 (M+H).

Example 11

5-(4-Aminobutoxy)-7-(4-dimethylaminophenyl)-[1,6]naphthyridine (Method D)

This example is illustrative of a procedure that may be used to prepare compounds with a substituted alkoxy in the 5-position.

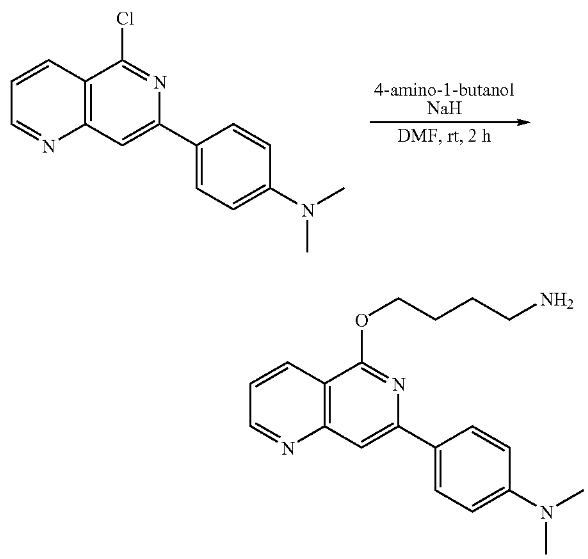

To a solution of 4-amino-1-butanol (100 μL, 1 mmol) in DMF (500 μL) was added sodium hydride (60% suspension in oil, 5 mg, 0.1 mmol), and the contents stirred at room temperature for 20 minutes. 5-Chloro-7-(4-dimethylaminophenyl)-[1,6]naphthyridine (Example 2) (15 mg, 50 μmol) was added, and the contents stirred at room temperature for 2 hours. Water (200 μL) was added to quench the reaction. Purification by preparative TLC plate developed using 10% 2 M ammonia-MeOH in dichloromethane afforded the title compound as a yellow solid (3 mg). MS calculated for $C_{20}H_{24}N_4O$ 336, found (M+H) 337 (100%).

Example 12

7-(4-Dimethylaminophenyl)-8-iodo-[1,6]naphthyridin-5-ol

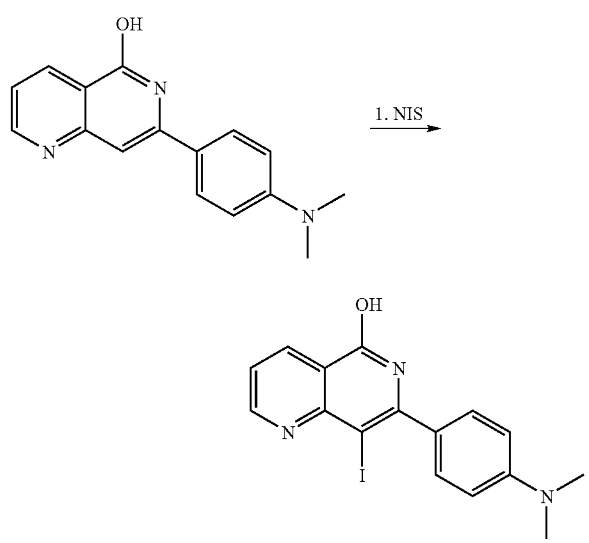

The following example illustrates how an iodo substituent may be introduced in the 8-position. Further synthetic modification of the iodo group by methods known to those skilled in the art may be carried out to obtain other desired substituents in the 8-position (see for instance, Example 13).

A solution of 7-(4-dimethylaminophenyl)-[1,6]naphthyridin-5-ol (Example 1)

(293 mg, 1.10 mmol) and N-iodosuccinimide (261 mg, 1.16 mmol) in DMF (7 mL) was stirred in the dark at room temperature for 4 hours. The solution was poured into dichloromethane (50 mL), washed with aqueous sodium bicarbonate (2×20 mL), dried over anhydrous magnesium sulfate and concentrated in vacuo to afford the title compound as a yellow solid (390 mg). $^1$H NMR ($CD_3OD$, 400 MHz) δ 8.95 (dd, 1H), 8.60 (dd, 1H), 7.53 (dd, 1H), 7.40 (d, 2H), 6.84 (d, 2H), 2.86 (s, 6H).

Example 13

8-Cyano-7-(4-dimethylaminophenyl)-[1,6]naphthyridin-5-ol

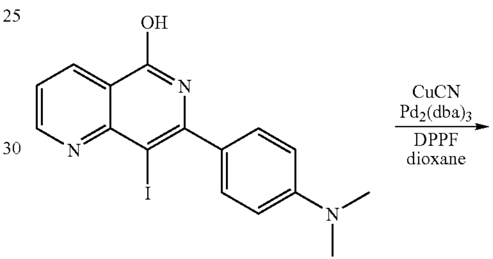

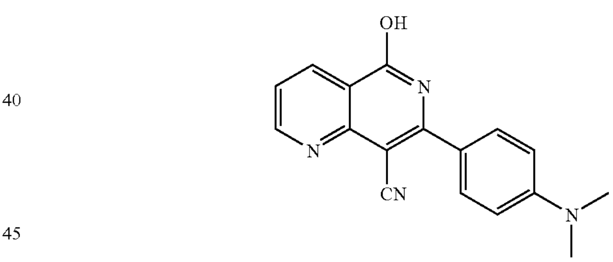

A solution of 7-(4-dimethylaminophenyl)-8-iodo-[1,6]naphthyridin-5-ol (Example 12) (134 mg, 0.34 mmol), cuprous cyanide (123 mg, 1.37 mmol), tris(dibenzylideneacetone)dipalladium (13 mg, 0.0136 mmol) and 1,1'-bis(diphenylphosphino)-ferrocene (30 mg, 0.054 mmol) in 1,4-dioxane (4 mL) was heated to 100° C. for 16 hours. The dark solution was allowed to cool to room temperature and EtOAc (10 mL) was added. This solution was poured through an extraction tube filled with diatomaceous earth loaded with saturated sodium bicarbonate solution, and a further 20 mL EtOAc was added to wash the tube. The combined organic extracts were concentrated in vacuo. Purification by flash chromatography eluting with 2.5% MeOH/dichloromethane afforded the title compound as a yellow solid (24 mg). $^1$H NMR (DMSO-d6, 400 MHz) δ 9.01 (dd, 1H), 8.52 (m, 1H), 7.64 (d, 2H), 7.59 (dd, 1H), 6.85 (d, 2H), 3.03 (s, 6H), MS (m/e) calculated for C17H14N4O 290, found (M+H) 291 (100%).

The cyano group may be modified by methods known in the art to obtain additional substituents in the 8-position. Intermediates may be converted to compounds of formula (I) by Methods B and C.

Example 14

7-(4-Methoxyphenyl)-[1,6]naphthyridin-5-ol (Method E)

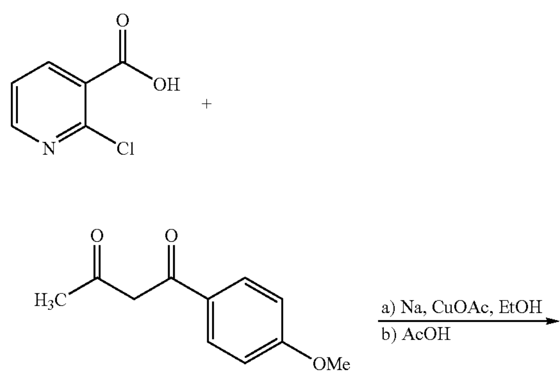

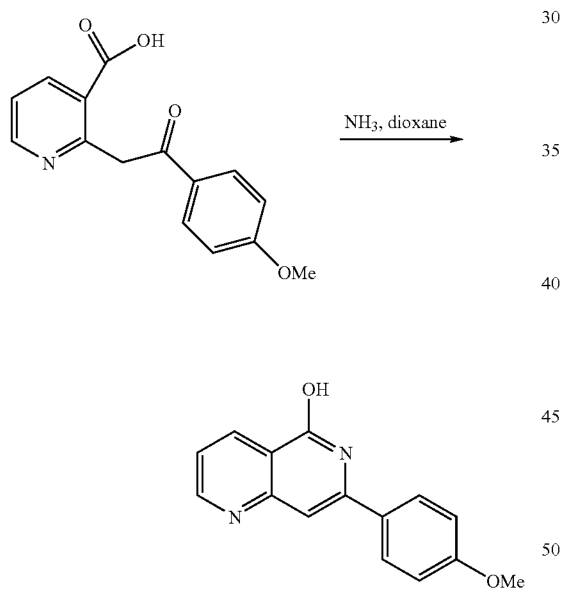

1-(4-Methoxyphenyl)acetylacetone (81 g, 0.5 mol) was added to a solution of NaOEt in EtOH (18.7 g Na in 400 mL abs. EtOH) at room temperature. Then 2-chloronicotinic acid (53.5 g) and CuOAc (2.7 g) in 100 mL of EtOH was added and the reaction was refluxed for 4 hours. The cooled solution was acidified with HOAc (330 mL). The material was purified by pouring into $CHCl_3$/MeOH, filtering and evaporating. The resultant solid was then washed with benzene to give 61.7 g (67%) 2-[2-(4-methoxyphenyl)-2-oxo-ethyl]-nicotinic acid, mp 158-163° C.

The above nicotinic acid derivative (20 g) was combined with dioxane (100 mL) and conc. $NH_3$ (200 mL) and heated to reflux. The product was washed with $H_2O$ and yielded 13.2 g (71%) of the title compound as a beige solid, mp 295-298° C.

Example 15

5-Chloro-7-(4-methoxyphenyl)-[1,6]naphthyridine (Method B)

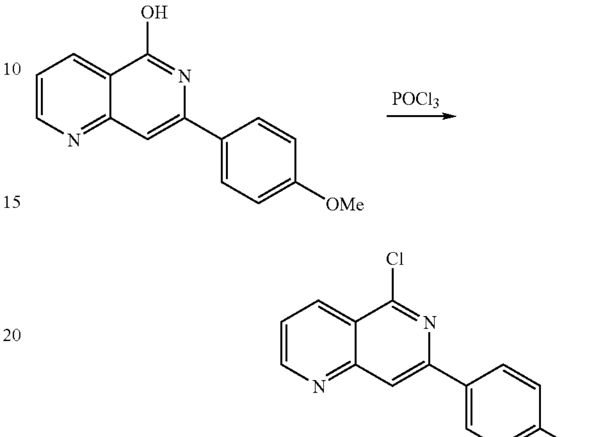

7-(4-Methoxyphenyl)-[1,6]naphthyridin-5-ol (13 g) and $POCl_3$ (275 mL) was heated to 135° C. for 26 hours in a sealed tube. The mixture was cooled and the $POCl_3$ was evaporated. The residue was poured onto ice and neutralized with 2M $Na_2CO_3$ and the precipitate was filtered and washed with $H_2O$ to yield 13.8 g of the title compound (98.5%), mp 126-127° C.

Example 16

5-(3-Aminoethylamino)-7-(4-methoxyphenyl)-[1,6] naphthyridine

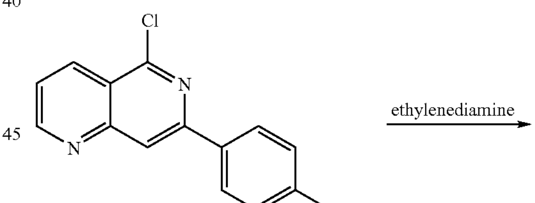

5-Chloro-7-(4-methoxyphenyl)-[1,6]naphthyridine (50 mg) was dissolved in ethylenediamine (1 mL) and heated to 140° C. for 16 hours. The mixture was concentrated and azeotroped with n-BuOH. The residue was treated with 1N NaOH (10 mL) and extracted with dichloromethane (2×50 mL). The product was purified by column chromatography (dichloromethane/MeOH 0 to 10%) to yield the title compound (20 mg, 92%), mp 134-136° C.

Example 17

7-(4-Methoxyphenyl)-[1,6]naphthyridin-5-yl]-methyl-amine (Method C)

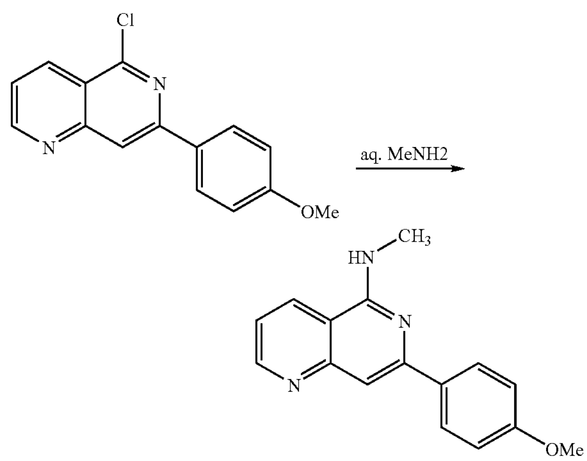

5-Chloro-7-(4-methoxyphenyl)-[1,6]naphthyridine (75 mg) was suspended in aqueous methylamine (0.8 mL) and heated to 150° C. for 18 hours. The mixture was concentrated and azeotroped with EtOH (2×25 mL). The residue was purified by column chromatography (dichloromethane/5% MeOH) and finally recrystallized from ether to yield the title compound (39 mg, 53%), mp 183-185° C.

Example 18

7-Phenyl-8-cyano-6H-[1,6]naphthyridin-5-one (Method E)

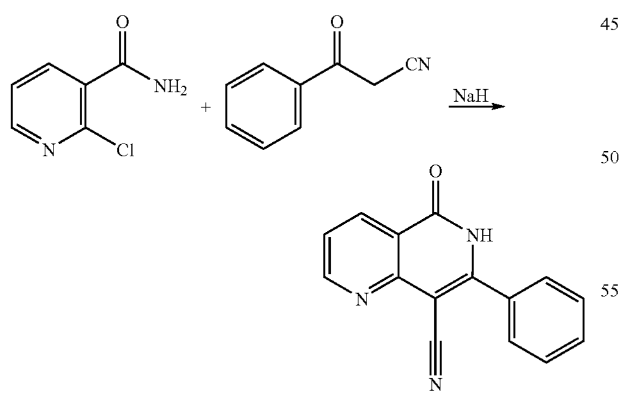

NaH (36 mg 1.5 mmol) was added in portions to anhydrous EtOH (4 mL) under $N_2$. After 30 minutes, benzoylacetonitrile (218 mg, 1. 5 mmol) was added, and the reaction mixture was allowed to stir under a nitrogen atmosphere for 30 minutes. 2-Chloronicotinamide (236 mg, 1.5 mmol) and CuOAc (36 mg, 0.3 mmol) were then added and the reaction mixture was heated to 50° C. The temperature was maintained for 10 days, after which time the reaction mixture was allowed to cool, was diluted with a 10% aqueous solution of $NH_4Cl$ (25 mL), and extracted with three portions of EtOAc (30 mL). The combined extracts were washed with brine, dried and evaporated to an oil which was triturated with $CH_2Cl_2$. The resulting solid (39 mg) was recrystallized from EtOH providing 30 mg (7.3%) of the title compound, mp 292-5° C.

Example 19

7-(4-Methoxyphenyl)-2-trifluoromethyl-[1,6]naphthyridin-5-ol (Method A)

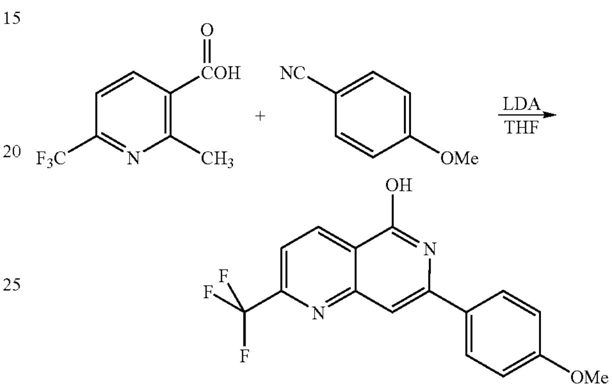

A solution of LDA (2.4 mmol) was prepared by adding n-BuLi (1.7 mL, 2.4 mmol, 1.4 M in hexanes) via syringe to a solution of diisopropylamine (247 mg, 2.4 mmol) in THF (10 mL) at 0° C. and stirring for 15 minutes. The solution was then cooled to −40° C., then 2-methyl-6-trifluoromethylnicotinic acid (250 mg, 1.2 mmol) in THF (5 mL) was added via syringe. After stirring at −40° C. for 30 minutes, 4-methoxybenzonitrile (162 mg, 1.2 mmol) in THF (5 mL) was added via syringe. The reaction mixture was allowed to warm to room temperature and stirred for 16 hours. The reaction was quenched by addition of sat. $NH_4Cl$ solution. A precipitate formed which was collected by vacuum filtration giving the title compond (150 mg, 40%) as an off white solid.

Example 20

5-Chloro-7-(4-methoxyphenyl)-2-trifluoromethyl-[1,6]naphthyridine (Method B)

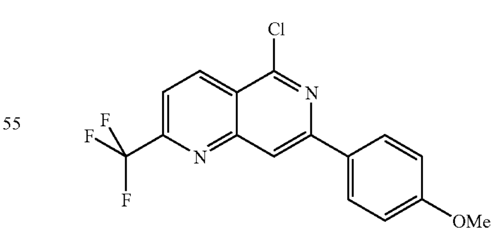

$POCl_3$ (3 mL) was added to 7-(4-methoxyphenyl)-2-trifluoromethyl-[1,6]naphthyridin-5-ol (Example 19) (125 mg, 0.4 mmol). The mixture was heated at 100° C. for 3 hours. The excess $POCl_3$ was concentrated under reduced pressure. The residue was diluted with $CH_2Cl_2$, washed with sat. $NaHCO_3$, dried over $Na_2SO_4$, and concentrated giving the title compound (73 mg, 55%) as an orange solid.

Example 21

5-(3-Aminopropylamino)-2-trifluoromethyl-7-(4-methoxyphenyl)-[1,6]naphthyridine (Method C)

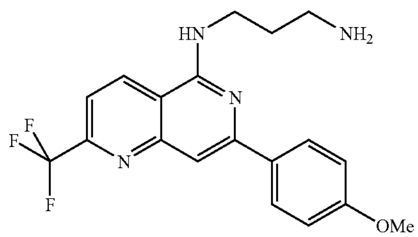

A mixture of 5-chloro-7-(4-methoxy-phenyl)-2-trifluoromethyl-[1,6]naphthyridine (55 mg, 0.2 mmol) and 1,3-diaminopropane (2.5 mL) in a sealed reaction vessel was heated at 100° C. for 3 hours. The mixture was diluted with toluene and concentrated three times to azeotropically remove excess 1,3-diaminopropane. The residue was diluted with EtOAc, washed sequentially with sat. $NaHCO_3$, $H_2O$, sat. NaCl, dried over $Na_2SO_4$, and concentrated giving the title compound (60 mg, quantitative) as a yellow solid.

Example 22

7-(4-Methoxyphenyl)-3-bromo-[1,6]naphthyridin-5-ol (Method E)

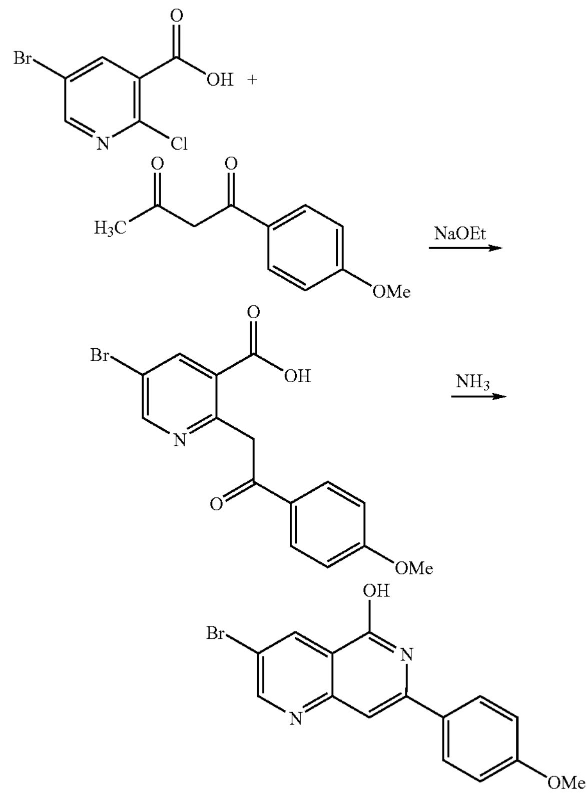

A solution of NaOEt (0.6 mmol) was prepared by adding Na (15 mg, 0.6 mmol) to EtOH (5 mL) and stirring at room temperature for 30 minutes. 1-(4-Methoxyphenyl)-butane-1,3-dione (121 mg, 0.6 mmol) was added and the mixture was stirred at room temperature for 15 minutes. Then 5-bromo-2-chloronicotinic acid (100 mg, 0.4 mmol) and CuOAc (10 mg, catalytic) was added. The mixture was then heated to reflux for 4 hours. The mixture was cooled to room temperature and quenched by addition of HOAc (0.5 mL). The mixture was concentrated, then diluted with EtOAc and washed with 1M NaOH (×2). The basic washings were acidified with 6N HCl (pH ~3). A precipitate formed and was collected by vacuum filtration giving after air drying 5-bromo-2-[2-(4-methoxyphenyl)-2-oxo-ethyl]-nicotinic acid (65 mg, 44%) as a light brown solid.

The above nicotinic acid derivative (310 mg, 0.5 mmol) in ethanolic ammonia (2 mL, 0.2M) was heated at 90° C. in a sealed reaction vessel for 20 hours. A precipitate formed upon cooling, and was collected by vacuum filtration giving the title compound (120 mg, 73%) as an off white solid.

Example 23

5-(3-Aminopropylamino)-3-bromo-7-(4-methoxyphenyl)-[1,6]naphthyridine (Methods B and C)

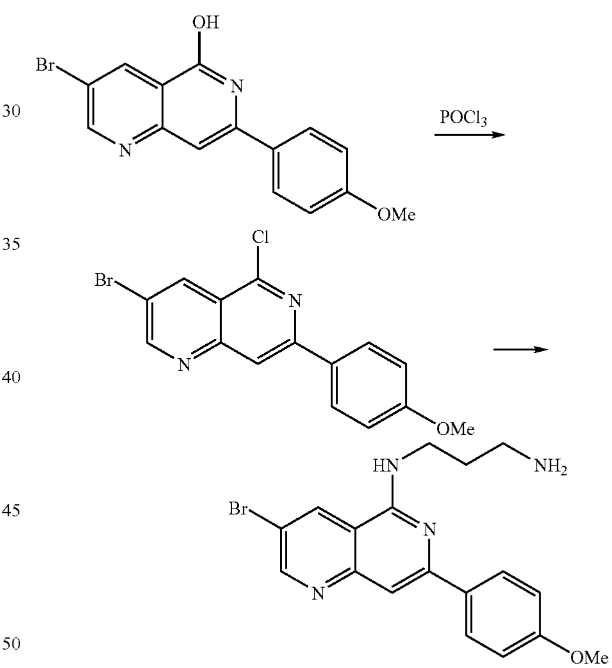

$POCl_3$ (3 mL) was added to 7-(4-methoxyphenyl)-3-bromo-[1,6]naphthyridin-5-ol (Example 22) (115 mg, 0.4 mmol). The mixture was heated at 100° C. for 3 hours. The excess $POCl_3$ was concentrated under reduced pressure. The residue was diluted with $CH_2Cl_2$, washed with sat. $NaHCO_3$, dried over $Na_2SO_4$, and concentrated giving 5-chloro-7-(4-methoxyphenyl)-3-bromo-[1,6]naphthyridine (115 mg, 94%) as a yellow solid.

A mixture of the above intermediate (98 mg, 0.3 mmol) and 1,3-diaminopropane (3 mL) in a sealed reaction vessel was heated at 100° C. for 3 hours. The mixture was diluted with toluene and concentrated three times to azeotropically remove excess 1,3-diaminopropane. The residue was triturated with 25% MeOH/$Et_2O$ giving the title compound (7 mg, 7%) as an orange solid.

Example 24

5-(3-Aminopropylamino)-7-(4-methoxyphenyl)-3-phenyl-[1,6]naphthyridine

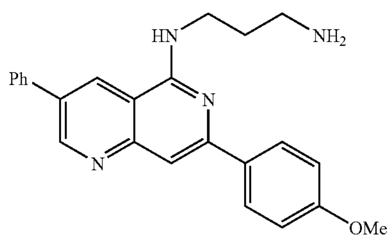

Argon gas was bubbled through a mixture of the product of Example 23 (68 mg, 0.2 mmol), $PhB(OH)_2$ (33 mg, 0.3 mmol), and $Pd(PPh_3)_4$ (25 mg, 0.02 mmol) in 2M $Na_2CO_3$ (1 mL)/EtOH (1 mL)/benzene (3 mL) for 10 minutes. The mixture was then heated to reflux for 20 hours. After cooling to room temperature the mixture was partitioned between EtOAc and $H_2O$. The organic material was washed with sat. NaCl, dried over $Na_2SO_4$, and concentrated. The crude residue was fractionated by column chromatography on silica gel (50% EtOAc/45% EtOH/5% $NH_4OH$) giving the title compound (10 mg, 15%) as a light yellow solid.

Example 25

2-Chloro-7-(4-methoxy-phenyl)-[1,6]naphthyridin-5-1 (Method F)

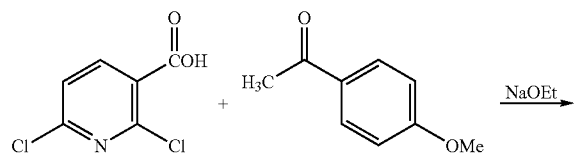

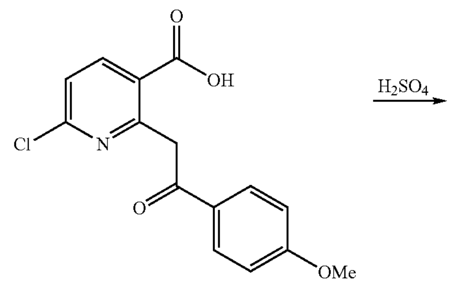

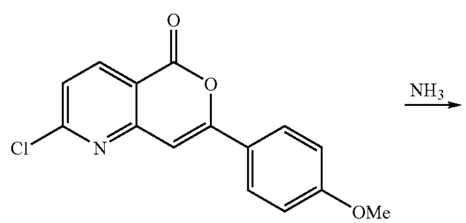

-continued

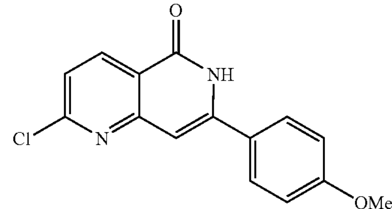

Elemental sodium (173 mg, 7.5 mmol) was added to 40 mL of absolute EtOH stirring under nitrogen. After all of the sodium reacted, 4-methoxyacetophenone (1.44 g, 7.5 mmol) was added, and the reaction stirred an additional 15 minutes. 2,6-Dichloronicotinic acid (1 g, 5.2 mmol) and copper acetate (80 mg, 0.65 mmol) was added and the reaction was stirred at reflux for 16 hours. The reaction was cooled to room temperature and quenched with 1 mL concentrated acetic acid. The mixture was concentrated to a solid, and redissolved in EtOAc. A small portion of fine inorganic precipitate was filtered off. The organic layer was extracted with 3×100 mL 1N NaOH. This was acidified with 1 N HCl to a pH of ~4. A precipitate formed and was collected by vacuum filtration, yielding 6-chloro-2-[2-(4-methoxyphenyl)-2-oxo-ethyl]-nicotinic acid (1 g, 63%) as a tan solid.

The above nicotinic acid derivative (1 g, 3.27 mmol) was dissolved in 50% aqueous sulfuric acid v/v (10 mL) and stirred at room temperature for 20 hours. The reaction started as a yellow solution, and a precipitate formed after an hour. The reaction was added to ice water and a fine yellow precipitate formed. This was collected by vacuum filtration, yielding 2-chloro-7-(4-methoxyphenyl)-pyrano[4,3-b]pyridin-5-one (876 mg, 93%) as a light yellow solid.

The above intermediate (225 mg, 0.78 mmol) and 2M ammonia in EtOH (15 mL) were combined and heated to 80° C. for 16 hours. A heavy white precipitate formed. Vacuum filtration yielded the title compound (164 mg, 73%) as a white solid.

Example 26

2,5-Bis-(Aminopropylamino)-7-(4-methoxyphenyl)-[1,6]naphthyridine

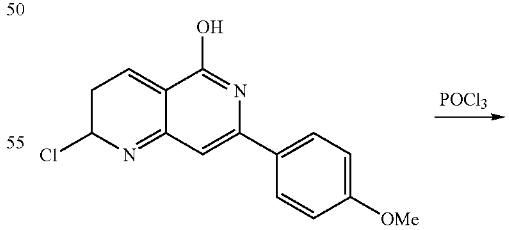

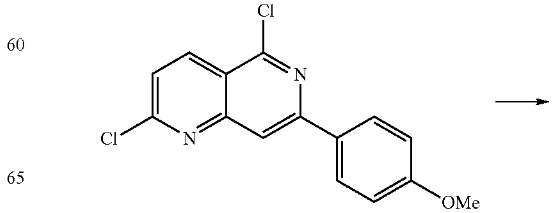

-continued

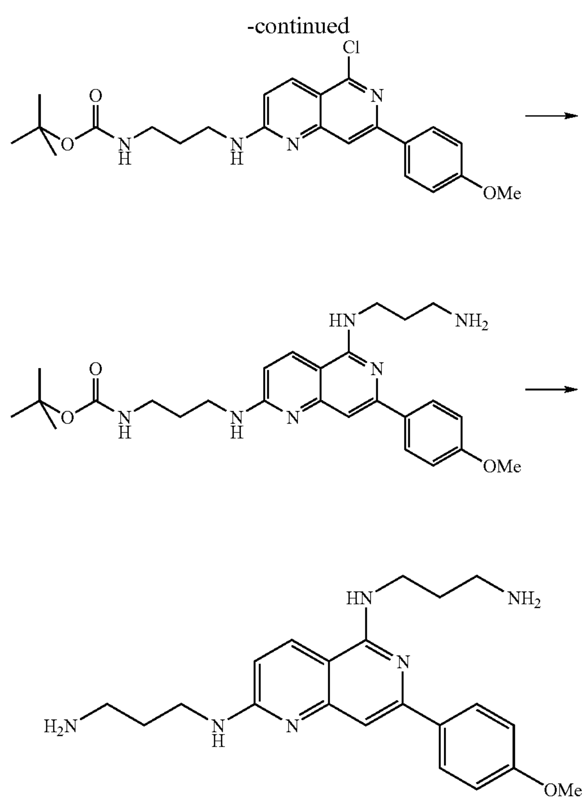

2-Chloro-7-(4-methoxyphenyl)-[1,6]naphthyridin-5-ol (135 mg, 0.47 mmol) was dissolved in phosphorus oxychloride (2 mL, 21.5 mmol) and refluxed for 3 hours. An orange solid precipitated. The reaction mixture was diluted with dichloromethane (25 mL) and concentrated to an orange solid. The solid was re-dissolved in EtOAc (300mL) and washed with saturated sodium bicarbonate solution (100 mL), brine (100 mL) and dried over magnesium sulfate. Filtration and concentration yielded 2,5-dichloro-7-(4-methoxy-phenyl)-[1,6]naphthyridine (138 mg, 86%) as a yellow solid.

The above intermediate (135 mg, 0.44 mmol), (3-amino-propyl)-carbamic acid tert-butyl ester (0.31 mL, 1.77 mmol), and diethyl propylamine (0.15 mL, 0.88 mmol) were combined in methoxyethanol (5 mL) and stirred at 120° C. for 16 hours. Column chromatography afforded {3-[5-chloro-7-(4-methoxyphenyl)-[1,6]naphthyridin-2-ylamino]-propyl}-carbamic acid tert-butyl ester (148 mg, 76%).

A mixture of the above intermediate (50 mg, 0.113 mmol) and 1,3-diaminopropane (1 mL, 12 mmol) in a sealed reaction vessel was heated at 115° C. for 3 hours. The mixture was diluted with toluene and concentrated three times to azeotropically remove excess 1,3-diaminopropane. The residue was triturated to a solid with ether and filtered. The product was purified on a preparatory TLC plate, providing {3-[5-(3-aminopropylamino)-7-(4-methoxyphenyl)-[1,6]naphthyridin-2-ylamino]-propyl}-carbamic acid tert-butyl ester (53 mg, 99%).

The above carbamic acid tert-butyl ester (50 mg, 0.104 mmol) was stirred in 4N HCl in dioxane (2 mL) for 4 hours. A fine precipitate formed which was filtered and re-dissolved in slightly acidic MeOH. Solid phase extraction on a Varian SCX cartridge (2 g) afforded the title compound (4 mg, 8%).

Example 27

5-(3-Aminopropylamino)-2-benzyloxy-7-(4-methoxyphenyl)-[1,6]naphthyridine

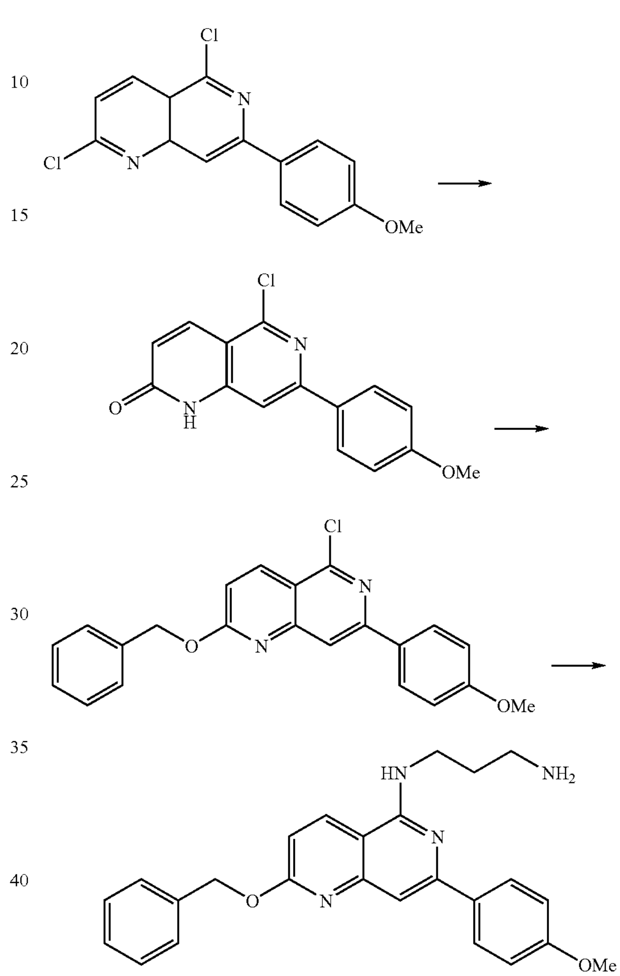

2,5-Dichloro-7-(4-methoxyphenyl)-[1,6]naphthyridine (Example 26) (700 mg, 2.29 mmol) was stirred in saturated sodium bicarbonate solution (100 mL) for 20 minutes. A white solid precipitated and was isolated by vacuum filtration to afford 5-chloro-7-(4-methoxy-phenyl)-1H-[1,6]naphthyridin-2-one (209 mg, 32%).

The above intermediate (100 mg, 0.35 mmol), benzyl bromide (0.05 mL, 0.42 mmol), and silver carbonate (115 mg, 0.42 mmol) were combined in THF (5 mL) and stirred at room temperature for 72 hours. The reaction mixture was filtered to remove inorganic salts, and concentrated to an oil. Column chromatography afforded 2-benzyloxy-5-chloro-7-(4-methoxyphenyl)-[1,6]naphthyridine (61 mg, 46%).

A mixture of the above intermediate (61 mg, 0.162 mmol), 1,3-diaminopropane (2 mL, 24 mmol), and methoxyethanol (2 mL) in a sealed reaction vessel was heated at 120° C. for 24 hours. The mixture was diluted with toluene and concentrated three times to azeotropically remove excess 1,3-diaminopropane. Column chromatography yielded the title compound (45 mg, 67%).

Example 28

5-(3-Aminopropylamino)-2-benzylamino-7-(4-methoxyphenyl)-[1,6]naphthyridine

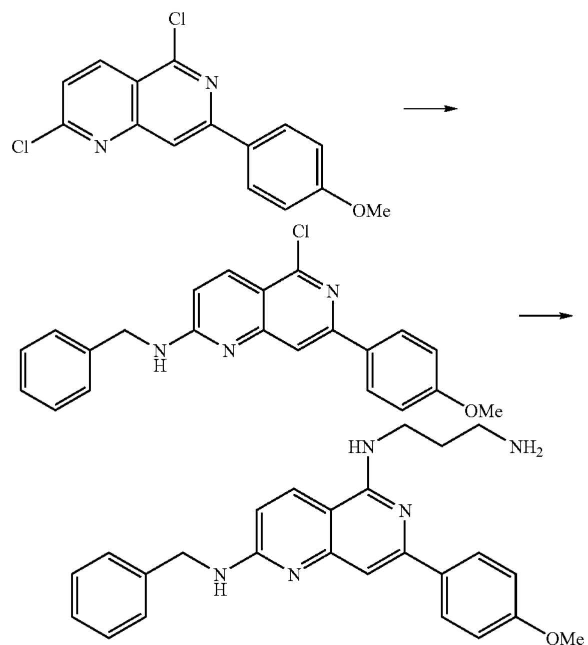

2,5-Dichloro-7-(4-methoxyphenyl)-[1,6]naphthyridine (147 mg, 0.48 mmol) and benzyl amine (0.055 mL, 0.5 mmol) were combined in methoxyethanol (2 mL) and stirred at 80° C. for 72 hours. The crude reaction mixture was concentrated, and column chromatography afforded benzyl-[5-chloro-7-(4-methoxyphenyl)-[1,6]naphthyridin-2-yl]-amine (55 mg, 30%).

A mixture of the above intermediate (50 mg, 0.133 mmol), 1,3-diaminopropane (2 mL, 24 mmol), and methoxyethanol (2 mL) in a sealed reaction vessel was heated at 120° C. for 24 hours. The mixture was diluted with toluene and concentrated three times to azeotropically remove excess 1,3-diaminopropane. Preparatory TLC afforded the title compound (46 mg, 83%).

Assessment of Biological Properties

The inhibition of SYK kinase was measured with the following assay.

SYK was purified as a GST-fusion protein. The kinase activity was measured using DELFIA (Dissociation Enhanced Lanthanide Fluoroimmunoassay) which utilizes europium chelate-labeled anti-phosphotyrosine antibodies to detect phosphate transfer to a random polymer, poly $Glu_4$:$Tyr_1$ (PGTYR).

The kinase assay was performed in kinase assay buffer (50 mM HEPES, pH 7.0, 25 mM $MgCl_2$, 5 mM $MnCl_2$, 50 mM KCl, 100 μM $Na_3VO_4$, 0.2% BSA, 0.01% CHAPS). Test samples initially dissolved in DMSO at 1 mg/mL, were prediluted for dose response (11 doses with starting final concentration of 30 μg/mL, 1 to 3.5 serial dilutions) with the assay buffer in 96-well polypropylene microtiter plates. A 25 μL aliquot of this diluted sample was added to neutravidin coated 96-well white plate (PIERCE). A 25 μL volume of diluted enzyme (0.6 ng/mL final conc.) and a 50 μL volume of a mixture of substrates containing 200 nM ATP and 3.6 ng/μL PGTYR-biotin (CIS Biointernational) in kinase buffer was sequentially added to the assay plates. Background wells were incubated with buffer, rather than 25 μL enzyme. The assay plates were incubated for 30 minutes at room temperature. Following incubation, the assay plates were washed three times with 300 μL wash buffer (50 mM Tris-HCL, pH 7.4, 150 mM NaCl, 0.05% Tween 20, 0.2% BSA). A 100 μL aliquot of europium-labeled anti-phosphotyrosine ($Eu^{3+}$-PT66, Wallac CR04-100) diluted in 50 mM Tris-HCl, pH 7.8, 150 mM NaCl, 10 μM DTPA, 0.05% Tween 40, 0.2% BSA, 0.05% BGG (1 nM final conc.) was added to each well and incubated for 30 minutes at room temperature. Upon completion of the incubation, the plate was washed four times with 300 μL of wash buffer and 100 μL of DELFIA Enhancement Solution (Wallac) was added to each well. After 10 minutes or longer, time-resolved fluorescence was measured on the LJL's Analyst (excitation at 360 nm, emission at 620 nm, EU 400 Dichroic Mirror) after a delay time of 250 μs.

Compounds of the invention including those in the Synthetic Examples section and those listed individually in the Detailed Description of the Invention section were evaluated for inhibition of SYK kinase in this assay. All had $IC_{50}$s below 30 μM, preferred compounds had $IC_{50}$s below 1 μM.

Methods of Therapeutic Use

The compounds of the invention are useful in inhibiting the activity of SYK kinase. In doing so, these compounds are useful in blocking disease processes mediated by SYK kinase. Compounds of the invention effectively block activation of mast cells by inhibiting SYK kinase. This in turn prevents the release of inflammatory mediators including histamine, proteases, leukotrienes and cytokines. These mediators play a key role in the etiology of allergic and inflammatory disorders. Preventing the release of these mediators is a desirable means for treating these conditions. Thus there are provided methods for treating these conditions using the compounds of the invention. These include inflammatory and allergic conditions involving mast cell activation, including but not limited to asthma, chronic obstructive pulmonary disease (COPD), adult respiratory distress syndrome (ARDS), ulcerative colitis, Crohn's disease bronchitis, conjunctivitis, psoriasis, scleroderma, urticaria, dermatitis and allergic rhinitis. They also include inflammatory conditions where B cells contribute to the etiology of the disease, including but not limited to lupus and rheumatoid arthritis. The compounds of the invention can also be used to treat other disorders associated with inappropriate mast cell or B cell activation, unrelated to those listed above or discussed in the Background of the Invention. Therefore, the invention also provides methods of treating allergic and inflammatory diseases comprising administering to a patient in need of such treatment a pharmaceutically effect amount of a compound according to the invention.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous. Compositions comprising the compounds of the invention for each of the aforementioned routes of administration will be apparent to the skilled artisan. The invention also provides for pharmaceutical compositions including a therapeutically effective amount of the compounds according to the invention. Such pharmaceutical compositions will include pharmaceutically acceptable carriers and adjuvants as further described below.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of the invention (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:

1. A method of making a compound of formula (I) below:

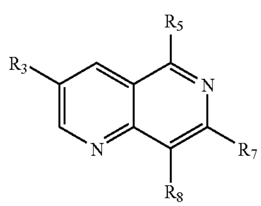

wherein $R_3$ is H, $C_{1-3}$alkyl, halogen or phenyl;

$R_5$ is $N(R_9)(R_{10})$ wherein $R_9$ is H or $C_{1-3}$alkyl;

$R_{10}$ is amino$C_{2-6}$alkyl, $C_{1-4}$alkylamino$C_{2-6}$alkyl, di$C_{1-4}$alkylamino$C_{2-6}$alkyl, $C_{1-4}$alkoxy$C_{2-6}$alkyl or hydroxy$C_{2-6}$alkyl, wherein one methylene group in said $C_{2-6}$alkyl is optionally replaced with an oxygen, sulfur, NH, or $NCH_3$, and wherein each methylene group in said $C_{2-6}$alkyl is optionally substituted with a halogen, cyano or hydroxy group, or $R_{10}$ is $C_{3-7}$cycloalkyl, heterocycloalkyl, heteroaryl, $C_{3-7}$cycloalkyl$C_{1-4}$alkyl, heterocycloalkyl$C_{1-4}$alkyl, aryl$C_{1-4}$alkyl or heteroaryl$C_{1-4}$alkyl each optionally substituted with one or more $C_{1-4}$alkyl, amino, $C_{1-4}$alkylamino, di$C_{1-4}$alkylamino, amino$C_{1-3}$alkyl, $C_{1-4}$alkylamino$C_{1-3}$alkyl, di$C_{1-4}$alkylamino$C_{1-3}$ alkyl, halogen, hydroxy, aminocarboxy or benzyl groups, or $R_9$ and $R_{10}$ together with the nitrogen they are bonded to may form a heterocycloalkyl group containing one or more heteroatoms which is optionally substituted with one or more $C_{1-4}$alkyl, amino, $C_{1-4}$alkylamino, di$C_{1-4}$alkylamino, amino$C_{1-3}$alkyl, $C_{1-4}$alkylamino$C_{1-3}$alkyl, di$C_{1-4}$alkylamino$C_{1-3}$ alkyl, halogen, hydroxy, aminocarboxy or benzyl groups;

$R_7$ is phenyl, naphthyl, furyl, thienyl, pyridyl, indolyl, benzothiazolyl or pyrrolyl optionally substituted with one or more $C_{1-3}$alkoxy, halogen, $CF_3$, $CF_3O$, hydroxy, $C_{1-3}$alkyl, amino, $C_{1-3}$alkylamino, di$C_{1-3}$alkylamino, $C_{1-3}$alkylamino$C_{1-3}$alkyl, di$C_{1-3}$alkylamino$C_{1-3}$alkyl, ($C_{1-3}$alkylamino$C_{1-3}$alkyl)($C_{0-3}$alkyl)amino, (di$C_{1-3}$ alkylamino$C_{1-3}$alkyl)($C_{0-3}$alkyl)amino, $C_{1-3}$alkylthio, aminocarboxy, $C_{1-3}$alkylcarbonyl, ureido optionally substituted with $C_{1-3}$alkyl, C(O)O$C_{1-4}$alkyl, C(O)OH, acetamido or heterocycloaklyl groups, or with a phenyl group which is optionally substituted with one or more $C_{1-3}$alkoxy, halogen, $CF_3$, $CF_3O$, hydroxy, $C_{1-3}$alkyl, amino, $C_{1-3}$alkylamino, di$C_{1-3}$alkylamino, $C_{1-3}$alkylamino$C_{1-3}$alkyl, di$C_{1-3}$alkylamino$C_{1-3}$alkyl, $C_{1-3}$alkylthio, aminocarboxy, $C_{1-3}$alkylcarbonyl, ureido optionally substituted with $C_{1-3}$alkyl, C(O)O$C_{1-4}$alkyl, C(O)OH, acetamido, heteroaryl or heterocycloalkyl groups; and $R_8$ is H;

with the proviso that $R_3$ is not hydrogen when $R_7$ is methoxy-subsituted phenyl and $R_5$ is

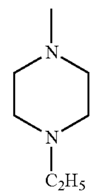

said method comprising:

(a) reacting the compound of formula (II) with a nitrile of the formula $R_7CN$ in the presence of a strong base in a suitable solvent to form a compound of formula (III):

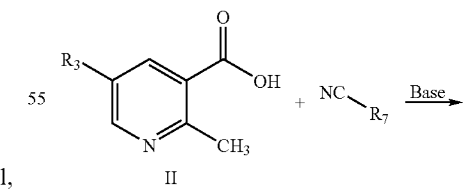

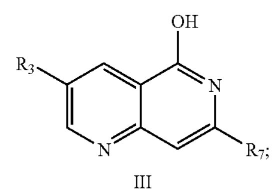

(b) reacting the compound of formula (III) with a suitable chlorinating agent to form the compound of formula (IV):

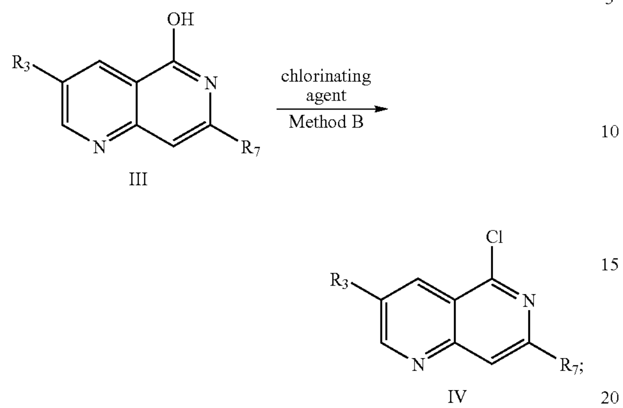

(c) reacting the compound of formula (IV) with an amine of the formula $HN(R_8)(R_9)$ to provide the desired compound of formula (I) wherein $R_5$ is $N(R_8)(R_9)$ and $R_8$ is H:

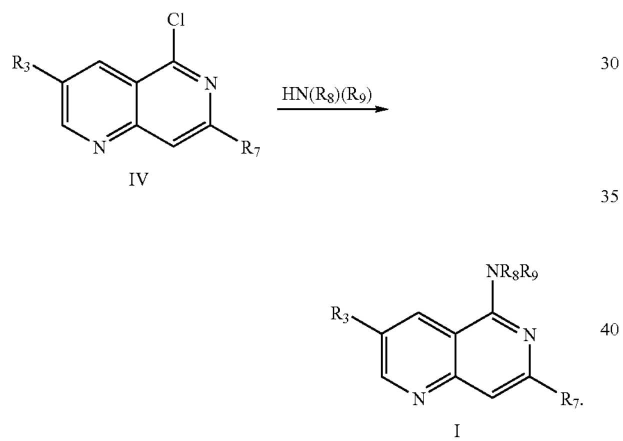

2. A method of making a compound of formula (I) below:

I

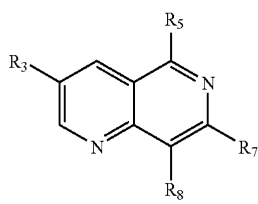

wherein $R_3$ is H, $C_{1-3}$alkyl, halogen or phenyl;

$R_5$ is $OR_{11}$ wherein $R_{11}$ is amino$C_{2-6}$alkyl, $C_{1-4}$alkylamino$C_{2-6}$alkyl, di$C_{1-4}$alkylamino$C_{2-6}$alkyl, $C_{1-4}$alkoxy$C_{2-6}$alkyl or hydroxy$C_{2-6}$alkyl, wherein one methylene group in said $C_{2-6}$alkyl is optionally replaced with an oxygen, sulfur, NH, or $NCH_3$, and wherein each methylene group in said $C_{2-6}$alkyl is optionally substituted with a halogen, cyano or hydroxy group, or $R_{11}$ is $C_{3-7}$cycloalkyl, heterocycloalkyl, heteroaryl, $C_{3-7}$cycloalkyl$C_{1-4}$alkyl, heterocycloalkyl$C_{1-4}$alkyl, aryl$C_{1-4}$alkyl or heteroaryl$C_{1-4}$alkyl each optionally substituted with one or more $C_{1-4}$alkyl, amino, $C_{1-4}$alkylamino, di$C_{1-4}$alkylamino, amino$C_{1-3}$alkyl, $C_{1-4}$alkylamino$C_{1-3}$alkyl, di$C_{1-4}$alkylamino$C_{1-3}$ alkyl, halogen, hydroxy, aminocarboxy or benzyl groups;

$R_7$ is phenyl, naphthyl, furyl, thienyl, pyridyl, indolyl, benzothiazolyl or pyrrolyl optionally substituted with one or more $C_{1-3}$alkoxy, halogen, $CF_3$, $CF_3O$, hydroxy, $C_{1-3}$alkyl, amino, $C_{1-3}$alkylamino, di$C_{1-3}$alkylamino, $C_{1-3}$alkylamino$C_{1-3}$alkyl, di$C_{1-3}$alkylamino$C_{1-3}$alkyl, ($C_{1-3}$alkylamino$C_{1-3}$alkyl)($C_{0-3}$alkyl)amino, (di$C_{1-3}$ alkylamino$C_{1-3}$alkyl)($C_{0-3}$alkyl)amino, $C_{1-3}$alkylthio, aminocarboxy, $C_{1-3}$alkylcarbonyl, ureido optionally substituted with $C_{1-3}$alkyl, C(O)O$C_{1-4}$alkyl, C(O)OH, acetamido or heterocycloaklyl groups, or with a phenyl group which is optionally substituted with one or more $C_{1-3}$alkoxy, halogen, $CF_3$, $CF_3O$, hydroxy, $C_{1-3}$alkyl, amino, $C_{1-3}$alkylamino, di$C_{1-3}$alkylamino, $C_{1-3}$alkylamino$C_{1-3}$alkyl, di$C_{1-3}$alkylamino$C_{1-3}$alkyl, $C_{1-3}$alkylthio, aminocarboxy, $C_{1-3}$alkylcarbonyl, ureido optionally substituted with $C_{1-3}$alkyl, C(O)O$C_{1-4}$alkyl, C(O) OH, acetamido, heteroaryl or heterocycloalkyl groups; and $R_8$ is H;

with the proviso that $R_3$ is not hydrogen when $R_7$ is methoxy-subsituted phenyl and $R_5$ is

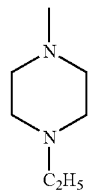

said method comprising:

(a) reacting the compound of formula (II) with a nitrile of the formula $R_7CN$ in the presence of a strong base in a suitable solvent to form a compound of formula (III):

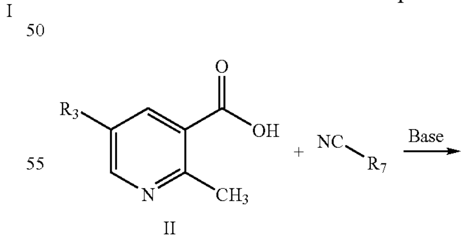

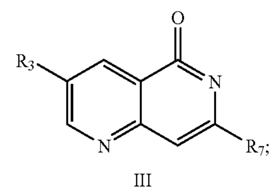

(b) reacting the compound of formula (III) with a suitable chlorinating agent to form the compound of formula (IV):
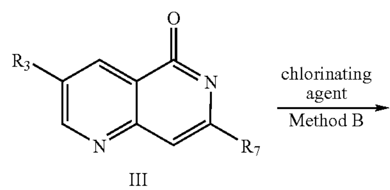
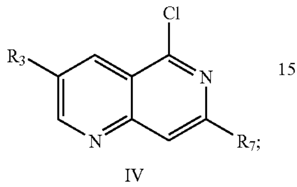
(c) reacting the compound of formula (IV) with an alcohol of the formula $HO(R_{10})$ in the presence of a suitable base in a suitable solvent to provide the desired compound of formula (I) wherein $R_5$ is $OR_{10}$ and $R_8$ is H:
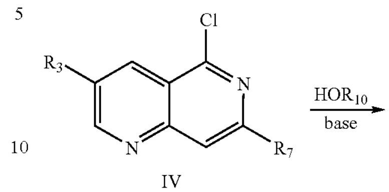
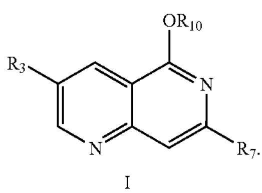
* * * * *